United States Patent
Weeber et al.

(10) Patent No.: US 11,327,210 B2
(45) Date of Patent: May 10, 2022

(54) NON-REPEATING ECHELETTES AND RELATED INTRAOCULAR LENSES FOR PRESBYOPIA TREATMENT

(71) Applicant: AMO Groningen B.V., Groningen (NL)

(72) Inventors: Hendrik A. Weeber, Groningen (NL); Robert Rosen, Groningen (NL)

(73) Assignee: AMO Groningen B.V., Groningen (NL)

( * ) Notice: Subject to any disclaimer, the term of this patent is extended or adjusted under 35 U.S.C. 154(b) by 498 days.

(21) Appl. No.: 16/022,599

(22) Filed: Jun. 28, 2018

(65) Prior Publication Data

US 2019/0004221 A1    Jan. 3, 2019

Related U.S. Application Data

(60) Provisional application No. 62/527,720, filed on Jun. 30, 2017.

(51) Int. Cl.
*A61F 2/16* (2006.01)
*G02B 5/18* (2006.01)
(Continued)

(52) U.S. Cl.
CPC .......... *G02B 5/1895* (2013.01); *A61F 2/1618* (2013.01); *A61F 2/1654* (2013.01);
(Continued)

(58) Field of Classification Search
CPC ........ G02C 7/04; G02C 7/06; G02C 2202/20; G02C 7/041; G02B 5/1895; G02B 3/10; G02B 27/0037; G02B 27/42–27/4216; G02B 27/58; A61F 2/1618; A61F 2/1654; A61F 2/145; A61F 2240/001; A61F 2/1656; G02F 2203/22
See application file for complete search history.

(56) References Cited

U.S. PATENT DOCUMENTS 3,367,734 A    2/1968  Karl et al.
3,722,986 A    3/1973  Tagnon
(Continued)

FOREIGN PATENT DOCUMENTS

AU    2005230194 B2    12/2010
CA        2501217 A1     4/2004
(Continued)

OTHER PUBLICATIONS

Albert D.M., "(Book Review) Intraocular Lenses: Evolution, Designs, Complications, and Pathology, by David Apple et al.," Archieves of Opthalmology, 1990, vol. 108, pp. 650.
(Continued)

*Primary Examiner* — Jennifer Dieterle
*Assistant Examiner* — Tiffany P Shipmon
(74) *Attorney, Agent, or Firm* — Johnson & Johnson Surgical Vision, Inc.

(57) ABSTRACT

Apparatuses, systems and methods for providing improved ophthalmic lenses, particularly intraocular lenses (IOLs). Exemplary ophthalmic lenses can include a plurality of echelettes arranged around the optical axis, having a profile in r-squared space. The echelettes may be non-repeating over the optical zone.

63 Claims, 12 Drawing Sheets

(51) Int. Cl.
   *G02C 7/04*       (2006.01)
   *G02C 7/06*       (2006.01)
   *A61F 2/14*       (2006.01)

(52) U.S. Cl.
   CPC ............... *G02C 7/04* (2013.01); *G02C 7/06* (2013.01); *A61F 2/145* (2013.01); *A61F 2240/001* (2013.01); *G02C 2202/20* (2013.01)

(56) References Cited

U.S. PATENT DOCUMENTS

| | | |
|---|---|---|
| 4,210,391 A | 7/1980 | Cohen |
| 4,340,283 A | 7/1982 | Cohen |
| 4,460,275 A | 7/1984 | Spriggs |
| 4,504,892 A | 3/1985 | Zulfilar |
| 4,504,982 A | 3/1985 | Burk |
| 4,580,883 A | 4/1986 | Shinohara |
| 4,606,626 A | 8/1986 | Shinohara |
| 4,637,697 A | 1/1987 | Freeman |
| 4,640,593 A | 2/1987 | Shinohara |
| 4,641,934 A | 2/1987 | Freeman |
| 4,642,112 A | 2/1987 | Freeman |
| 4,655,565 A | 4/1987 | Freeman |
| 4,710,193 A | 12/1987 | Volk |
| 4,762,408 A | 8/1988 | Shinohara |
| 4,778,462 A | 10/1988 | Grendahl |
| 4,795,462 A | 1/1989 | Grendahl |
| 4,798,608 A | 1/1989 | Grendahl |
| 4,798,609 A | 1/1989 | Grendahl |
| 4,856,234 A | 8/1989 | Goins |
| 4,856,889 A | 8/1989 | Guilino et al. |
| 4,881,804 A | 11/1989 | Cohen |
| 4,881,805 A | 11/1989 | Cohen |
| 4,898,461 A | 2/1990 | Portney |
| 4,932,970 A | 6/1990 | Portney |
| 4,936,666 A | 6/1990 | Futhey |
| 4,957,506 A | 9/1990 | Mercier |
| 4,978,211 A | 12/1990 | Cornu et al. |
| 4,995,714 A | 2/1991 | Cohen |
| 4,995,715 A | 2/1991 | Cohen |
| 5,016,977 A | 5/1991 | Baude et al. |
| 5,017,000 A | 5/1991 | Cohen |
| 5,019,098 A | 5/1991 | Mercier |
| 5,050,981 A | 9/1991 | Roffman |
| 5,054,905 A | 10/1991 | Cohen |
| 5,056,908 A | 10/1991 | Cohen |
| 5,061,058 A | 10/1991 | Guilino et al. |
| 5,066,301 A | 11/1991 | Wiley |
| 5,076,684 A | 12/1991 | Simpson et al. |
| 5,089,023 A | 2/1992 | Swanson |
| 5,089,024 A | 2/1992 | Christie et al. |
| 5,096,285 A | 3/1992 | Silberman |
| 5,100,226 A | 3/1992 | Freeman |
| 5,104,212 A | 4/1992 | Taboury et al. |
| 5,112,351 A | 5/1992 | Christie et al. |
| 5,114,220 A | 5/1992 | Baude et al. |
| 5,116,111 A | 5/1992 | Simpson et al. |
| 5,117,306 A | 5/1992 | Cohen |
| 5,120,120 A | 6/1992 | Cohen |
| 5,121,979 A | 6/1992 | Cohen |
| 5,121,980 A | 6/1992 | Cohen |
| 5,129,718 A | 7/1992 | Futhey et al. |
| 5,144,483 A | 9/1992 | Cohen |
| 5,148,205 A | 9/1992 | Guilino et al. |
| 5,161,057 A | 11/1992 | Johnson |
| 5,173,723 A | 12/1992 | Volk et al. |
| 5,178,636 A | 1/1993 | Silberman |
| 5,191,366 A | 3/1993 | Kashiwagi |
| 5,220,359 A | 6/1993 | Roffman |
| 5,225,858 A | 7/1993 | Portney |
| 5,229,797 A | 7/1993 | Futhey et al. |
| 5,236,970 A | 8/1993 | Christ et al. |
| 5,257,132 A | 10/1993 | Ceglio et al. |
| 5,260,727 A | 11/1993 | Oksman et al. |
| 5,322,649 A | 6/1994 | Rheinish et al. |
| 5,344,447 A | 9/1994 | Swanson |
| 5,349,394 A | 9/1994 | Freeman et al. |
| 5,349,471 A | 9/1994 | Morris et al. |
| 5,381,190 A | 1/1995 | Rehse et al. |
| 5,384,606 A | 1/1995 | Koch et al. |
| 5,408,281 A | 4/1995 | Zhang |
| 5,443,506 A | 8/1995 | Garabet |
| 5,443,507 A | 8/1995 | Jacobi |
| 5,444,106 A | 8/1995 | Zhou et al. |
| 5,446,508 A | 8/1995 | Kitchen |
| 5,448,312 A | 9/1995 | Roffman et al. |
| 5,485,228 A | 1/1996 | Roffman et al. |
| 5,581,405 A | 12/1996 | Meyers et al. |
| 5,589,982 A | 12/1996 | Faklis et al. |
| 5,629,800 A | 5/1997 | Hamblen |
| 5,652,638 A | 7/1997 | Roffman et al. |
| 5,674,284 A | 10/1997 | Chang et al. |
| 5,682,223 A | 10/1997 | Menezes et al. |
| 5,683,457 A | 11/1997 | Gupta et al. |
| 5,684,560 A | 11/1997 | Roffman et al. |
| 5,684,595 A | 11/1997 | Kato et al. |
| 5,699,142 A | 12/1997 | Lee et al. |
| 5,715,031 A | 2/1998 | Roffman et al. |
| 5,715,091 A | 2/1998 | Meyers |
| 5,724,258 A | 3/1998 | Roffman |
| 5,728,156 A | 3/1998 | Gupta et al. |
| 5,748,282 A | 5/1998 | Freeman |
| 5,760,871 A | 6/1998 | Kosoburd et al. |
| 5,777,719 A | 7/1998 | Williams et al. |
| 5,796,462 A | 8/1998 | Roffman et al. |
| 5,800,532 A | 9/1998 | Lieberman |
| 5,805,260 A | 9/1998 | Roffman et al. |
| 5,822,091 A | 10/1998 | Baker |
| 5,838,496 A | 11/1998 | Maruyama et al. |
| 5,847,802 A | 12/1998 | Menezes et al. |
| 5,888,122 A | 3/1999 | Gupta et al. |
| 5,895,422 A | 4/1999 | Hauber |
| 5,895,610 A | 4/1999 | Chang et al. |
| 5,929,969 A | 7/1999 | Roffman |
| 5,968,094 A | 10/1999 | Werblin et al. |
| 5,968,095 A | 10/1999 | Norrby |
| 5,982,543 A | 11/1999 | Fiala |
| 6,007,747 A | 12/1999 | Blake et al. |
| 6,019,472 A | 2/2000 | Koester et al. |
| 6,050,687 A | 4/2000 | Bille et al. |
| 6,070,980 A | 6/2000 | Obara et al. |
| 6,082,856 A | 7/2000 | Dunn et al. |
| 6,086,204 A | 7/2000 | Magnante |
| 6,089,711 A | 7/2000 | Blankenbecler et al. |
| 6,095,651 A | 8/2000 | Williams et al. |
| 6,120,148 A | 9/2000 | Fiala et al. |
| 6,126,283 A | 10/2000 | Wen et al. |
| 6,126,286 A | 10/2000 | Portney |
| 6,139,145 A | 10/2000 | Israel |
| 6,142,625 A | 11/2000 | Sawano et al. |
| 6,145,987 A | 11/2000 | Baude et al. |
| 6,154,323 A | 11/2000 | Kamo |
| 6,199,986 B1 | 3/2001 | Williams et al. |
| 6,210,005 B1 | 4/2001 | Portney |
| 6,215,096 B1 | 4/2001 | Von Wallfeld et al. |
| 6,224,211 B1 | 5/2001 | Gordon |
| 6,231,603 B1 | 5/2001 | Lang et al. |
| 6,270,220 B1 | 8/2001 | Keren |
| 6,271,915 B1 | 8/2001 | Frey et al. |
| 6,325,510 B1 | 12/2001 | Golub et al. |
| 6,338,559 B1 | 1/2002 | Williams et al. |
| 6,353,503 B1 | 3/2002 | Spitzer et al. |
| 6,413,276 B1 | 7/2002 | Werblin |
| 6,429,972 B1 | 8/2002 | Ota et al. |
| 6,439,720 B1 | 8/2002 | Graves et al. |
| 6,457,826 B1 | 10/2002 | Lett |
| 6,462,874 B1 | 10/2002 | Soskind |
| 6,464,355 B1 | 10/2002 | Gil |
| 6,474,814 B1 | 11/2002 | Griffin |
| 6,488,708 B2 | 12/2002 | Sarfarazi |
| 6,491,721 B2 | 12/2002 | Freeman et al. |
| 6,497,483 B2 | 12/2002 | Frey et al. |
| 6,511,180 B2 | 1/2003 | Guirao et al. |
| 6,520,638 B1 | 2/2003 | Roffman et al. |

(56) References Cited

U.S. PATENT DOCUMENTS

| | | |
|---|---|---|
| 6,527,389 B2 | 3/2003 | Portney |
| 6,533,416 B1 | 3/2003 | Fermigier et al. |
| 6,536,899 B1 | 3/2003 | Fiala |
| 6,537,317 B1 | 3/2003 | Steinert et al. |
| 6,547,391 B2 | 4/2003 | Ross, III et al. |
| 6,547,822 B1 | 4/2003 | Lang |
| 6,554,425 B1 | 4/2003 | Roffman et al. |
| 6,554,859 B1 | 4/2003 | Lang et al. |
| 6,557,992 B1 | 5/2003 | Dwyer et al. |
| 6,576,012 B2 | 6/2003 | Lang |
| 6,582,076 B1 | 6/2003 | Roffman et al. |
| 6,585,375 B2 | 7/2003 | Donitzky et al. |
| 6,609,673 B1 | 8/2003 | Johnson |
| 6,609,793 B2 | 8/2003 | Norrby et al. |
| 6,616,275 B1 | 9/2003 | Dick et al. |
| 6,655,802 B2 | 12/2003 | Zimmermann et al. |
| 6,685,315 B1 | 2/2004 | De Carle |
| 6,705,729 B2 | 3/2004 | Piers et al. |
| 6,709,103 B1 | 3/2004 | Roffman et al. |
| 6,755,524 B2 | 6/2004 | Rubinstein et al. |
| 6,791,754 B2 | 9/2004 | Ogawa |
| 6,802,605 B2 | 10/2004 | Cox et al. |
| 6,808,262 B2 | 10/2004 | Chapoy et al. |
| 6,818,158 B2 | 11/2004 | Pham et al. |
| 6,827,444 B2 | 12/2004 | Williams et al. |
| 6,830,332 B2 | 12/2004 | Piers et al. |
| 6,835,204 B1 | 12/2004 | Stork et al. |
| 6,846,326 B2 | 1/2005 | Zadno-Azizi et al. |
| 6,848,790 B1 | 2/2005 | Dick et al. |
| 6,851,803 B2 | 2/2005 | Wooley et al. |
| 6,884,261 B2 | 4/2005 | Zadno-Azizi et al. |
| 6,923,539 B2 | 8/2005 | Simpson et al. |
| 6,923,540 B2 | 8/2005 | Ye et al. |
| 6,951,391 B2 | 10/2005 | Morris et al. |
| 6,957,891 B2 | 10/2005 | Fiala |
| 6,972,032 B2 | 12/2005 | Aharoni et al. |
| 6,986,578 B2 | 1/2006 | Jones |
| 7,025,456 B2 | 4/2006 | Morris et al. |
| 7,036,931 B2 | 5/2006 | Lindacher et al. |
| 7,048,759 B2 | 5/2006 | Bogaert et al. |
| 7,048,760 B2 | 5/2006 | Cumming |
| 7,061,693 B2 | 6/2006 | Zalevsky |
| 7,073,906 B1 | 7/2006 | Portney |
| 7,093,938 B2 | 8/2006 | Morris et al. |
| 7,111,938 B2 | 9/2006 | Andino et al. |
| 7,137,702 B2 | 11/2006 | Piers et al. |
| 7,156,516 B2 | 1/2007 | Morris et al. |
| 7,159,983 B2 | 1/2007 | Menezes et al. |
| 7,188,949 B2 | 3/2007 | Bandhauer et al. |
| 7,198,640 B2 | 4/2007 | Nguyen |
| 7,217,375 B2 | 5/2007 | Lai |
| 7,221,513 B2 | 5/2007 | Cho et al. |
| 7,232,218 B2 | 6/2007 | Morris et al. |
| 7,287,852 B2 | 10/2007 | Fiala |
| 7,293,873 B2 | 11/2007 | Dai et al. |
| 7,365,917 B2 | 4/2008 | Zalevsky |
| 7,377,640 B2 | 5/2008 | Piers et al. |
| 7,377,641 B2 | 5/2008 | Piers et al. |
| 7,441,894 B2 | 10/2008 | Zhang et al. |
| 7,455,404 B2 | 11/2008 | Bandhauer et al. |
| 7,475,986 B2 | 1/2009 | Dai et al. |
| 7,481,532 B2 | 1/2009 | Hong et al. |
| 7,543,937 B2 | 6/2009 | Piers et al. |
| 7,572,007 B2 | 8/2009 | Simpson |
| 7,604,350 B2 | 10/2009 | Dursteler et al. |
| 7,615,073 B2 | 11/2009 | Deacon et al. |
| 7,654,667 B2 | 2/2010 | Blum et al. |
| 7,670,371 B2 | 3/2010 | Piers et al. |
| 7,677,725 B2 | 3/2010 | Piers et al. |
| 7,717,558 B2 | 5/2010 | Hong et al. |
| 7,753,521 B2 | 7/2010 | Wooley et al. |
| 7,871,162 B2 | 1/2011 | Weeber |
| 7,883,207 B2 | 2/2011 | Iyer et al. |
| 7,896,916 B2 | 3/2011 | Piers et al. |
| 7,922,326 B2 | 4/2011 | Bandhauer et al. |
| 7,984,990 B2 | 7/2011 | Bandhauer et al. |
| 7,998,198 B2 | 8/2011 | Angelopoulos et al. |
| 8,128,222 B2 | 3/2012 | Portney |
| 8,157,374 B2 | 4/2012 | Bandhauer et al. |
| 8,192,022 B2 | 6/2012 | Zalevsky |
| 8,197,063 B2 | 6/2012 | Iyer et al. |
| 8,216,307 B2 | 7/2012 | Schaper, Jr. |
| 8,231,219 B2 | 7/2012 | Weeber |
| 8,231,673 B2 | 7/2012 | Sacharoff et al. |
| 8,235,525 B2 | 8/2012 | Lesage et al. |
| 8,240,850 B2 | 8/2012 | Apter et al. |
| 8,262,728 B2 | 9/2012 | Zhang et al. |
| 8,292,953 B2 | 10/2012 | Weeber et al. |
| 8,382,281 B2 | 2/2013 | Weeber |
| 8,388,137 B2 | 3/2013 | Dreher et al. |
| 8,430,508 B2 | 4/2013 | Weeber |
| 8,444,267 B2 | 5/2013 | Weeber et al. |
| 8,480,228 B2 | 7/2013 | Weeber |
| 8,500,805 B2 | 8/2013 | Kobayashi et al. |
| 8,506,075 B2 | 8/2013 | Bandhauer et al. |
| 8,529,623 B2 | 9/2013 | Piers et al. |
| 8,556,416 B2 | 10/2013 | Lawu |
| 8,556,417 B2 | 10/2013 | Das et al. |
| 8,573,775 B2 | 11/2013 | Weeber |
| 8,619,362 B2 | 12/2013 | Portney |
| 8,636,796 B2 | 1/2014 | Houbrechts et al. |
| 8,652,205 B2 | 2/2014 | Hong et al. |
| 8,678,583 B2 | 3/2014 | Cohen |
| 8,709,079 B2 | 4/2014 | Zhang et al. |
| 8,734,511 B2 | 5/2014 | Weeber et al. |
| 8,740,978 B2 | 6/2014 | Weeber et al. |
| 8,747,466 B2 | 6/2014 | Weeber et al. |
| 8,755,117 B2 | 6/2014 | Kobayashi et al. |
| 8,771,348 B2 | 7/2014 | Zhao |
| 8,827,446 B2 | 9/2014 | Iyer et al. |
| 8,906,089 B2 | 12/2014 | Piers et al. |
| 9,069,185 B2 | 6/2015 | Zhao |
| 9,078,745 B2 | 7/2015 | Zhang et al. |
| 9,122,074 B2 | 9/2015 | Piers et al. |
| 9,164,201 B2 | 10/2015 | Fermigier et al. |
| 9,223,148 B2 | 12/2015 | Fiala et al. |
| 9,304,329 B2 | 4/2016 | Zhao |
| 9,310,624 B2 | 4/2016 | Argal et al. |
| 9,320,594 B2 | 4/2016 | Schwiegerling |
| 9,329,309 B2 | 5/2016 | Van Heugten |
| 9,335,563 B2 | 5/2016 | Weeber |
| 9,335,564 B2 | 5/2016 | Choi et al. |
| 9,370,416 B2 | 6/2016 | Argal et al. |
| 9,518,864 B2 | 12/2016 | Grossinger et al. |
| 9,563,070 B2 | 2/2017 | Ando et al. |
| 9,622,856 B2 | 4/2017 | Weeber et al. |
| 9,869,580 B2 | 1/2018 | Grossinger et al. |
| 9,925,041 B2 | 3/2018 | Gerlach et al. |
| 9,931,200 B2 | 4/2018 | Van Der Mooren et al. |
| 2001/0018612 A1 | 8/2001 | Carson et al. |
| 2002/0082690 A1 | 6/2002 | Sarbadhikari |
| 2002/0093701 A1 | 7/2002 | Zhang et al. |
| 2002/0105617 A1 | 8/2002 | Norrby et al. |
| 2002/0118337 A1 | 8/2002 | Perrott et al. |
| 2002/0122153 A1 | 9/2002 | Piers et al. |
| 2003/0014107 A1 | 1/2003 | Reynard |
| 2003/0063254 A1 | 4/2003 | Piers et al. |
| 2003/0076478 A1 | 4/2003 | Cox |
| 2003/0169491 A1 | 9/2003 | Bender et al. |
| 2003/0171808 A1 | 9/2003 | Phillips |
| 2004/0021824 A1 | 2/2004 | Ye et al. |
| 2004/0080710 A1 | 4/2004 | Wooley et al. |
| 2004/0085515 A1 | 5/2004 | Roffman et al. |
| 2004/0088050 A1 | 5/2004 | Norrby et al. |
| 2004/0106992 A1 | 6/2004 | Lang et al. |
| 2004/0111153 A1 | 6/2004 | Woods et al. |
| 2004/0138746 A1 | 7/2004 | Aharoni et al. |
| 2004/0150789 A1 | 8/2004 | Jones |
| 2004/0156014 A1 | 8/2004 | Piers et al. |
| 2004/0169820 A1 | 9/2004 | Dai et al. |
| 2004/0189981 A1 | 9/2004 | Ross et al. |
| 2004/0230299 A1 | 11/2004 | Simpson et al. |
| 2004/0246440 A1 | 12/2004 | Andino et al. |
| 2004/0252274 A1 | 12/2004 | Morris et al. |

(56) References Cited

U.S. PATENT DOCUMENTS

| | | |
|---|---|---|
| 2005/0057720 A1 | 3/2005 | Morris et al. |
| 2005/0096226 A1 | 5/2005 | Stock et al. |
| 2005/0099589 A1 | 5/2005 | Ishak |
| 2005/0128432 A1 | 6/2005 | Altmann |
| 2005/0203619 A1 | 9/2005 | Altmann |
| 2005/0259222 A1 | 11/2005 | Kelch et al. |
| 2005/0264757 A1 | 12/2005 | Morris et al. |
| 2005/0267575 A1 | 12/2005 | Nguyen et al. |
| 2006/0004446 A1 | 1/2006 | Aharoni et al. |
| 2006/0009816 A1 | 1/2006 | Fang et al. |
| 2006/0030938 A1 | 2/2006 | Altmann |
| 2006/0034003 A1 | 2/2006 | Zalevsky |
| 2006/0055883 A1 | 3/2006 | Morris et al. |
| 2006/0066808 A1 | 3/2006 | Blum et al. |
| 2006/0098162 A1 | 5/2006 | Bandhauer et al. |
| 2006/0098163 A1 | 5/2006 | Bandhauer et al. |
| 2006/0109421 A1 | 5/2006 | Ye et al. |
| 2006/0116763 A1 | 6/2006 | Simpson |
| 2006/0116764 A1 | 6/2006 | Simpson |
| 2006/0139570 A1 | 6/2006 | Blum et al. |
| 2006/0176572 A1 | 8/2006 | Fiala |
| 2006/0238702 A1 | 10/2006 | Glick et al. |
| 2006/0244904 A1 | 11/2006 | Hong et al. |
| 2006/0244905 A1 | 11/2006 | Piers et al. |
| 2007/0002444 A1 | 1/2007 | Piers et al. |
| 2007/0052920 A1 | 3/2007 | Stewart et al. |
| 2007/0129803 A1 | 6/2007 | Cumming et al. |
| 2007/0171362 A1 | 7/2007 | Simpson et al. |
| 2007/0182924 A1 | 8/2007 | Hong et al. |
| 2007/0236769 A1 | 10/2007 | Zalevsky |
| 2007/0258143 A1 | 11/2007 | Portney |
| 2007/0268451 A1 | 11/2007 | Raghuprasad |
| 2007/0282438 A1 | 12/2007 | Hong et al. |
| 2008/0030677 A1 | 2/2008 | Simpson |
| 2008/0147185 A1 | 6/2008 | Hong et al. |
| 2008/0161913 A1 | 7/2008 | Brady et al. |
| 2008/0161914 A1 | 7/2008 | Brady et al. |
| 2008/0269891 A1 | 10/2008 | Hong et al. |
| 2008/0273169 A1 | 11/2008 | Blum et al. |
| 2008/0300679 A1 | 12/2008 | Altmann |
| 2009/0062911 A1 | 3/2009 | Bogaert |
| 2009/0088840 A1 | 4/2009 | Simpson et al. |
| 2009/0164008 A1 | 6/2009 | Hong et al. |
| 2009/0187242 A1 | 7/2009 | Weeber et al. |
| 2009/0195748 A1* | 8/2009 | Bandhauer ............ A61F 2/1654 351/159.47 |
| 2009/0210054 A1 | 8/2009 | Weeber et al. |
| 2009/0234448 A1 | 9/2009 | Weeber et al. |
| 2009/0240328 A1 | 9/2009 | Treushnikov et al. |
| 2009/0268155 A1* | 10/2009 | Weeber ................. G02C 7/044 351/159.05 |
| 2009/0295295 A1 | 12/2009 | Shannon et al. |
| 2009/0323020 A1 | 12/2009 | Zhao et al. |
| 2010/0014049 A1 | 1/2010 | Bandhauer et al. |
| 2010/0016961 A1 | 1/2010 | Hong et al. |
| 2010/0057202 A1 | 3/2010 | Bogaert |
| 2010/0087921 A1 | 4/2010 | Simpson |
| 2010/0097569 A1 | 4/2010 | Weeber et al. |
| 2010/0100177 A1 | 4/2010 | Zhao |
| 2010/0131060 A1 | 5/2010 | Simpson et al. |
| 2010/0161048 A1 | 6/2010 | Schaper, Jr. |
| 2010/0161051 A1 | 6/2010 | Hong |
| 2010/0274233 A1 | 10/2010 | Dick et al. |
| 2010/0281021 A1 | 11/2010 | Weeber et al. |
| 2010/0312336 A1 | 12/2010 | Hong et al. |
| 2010/0321635 A1 | 12/2010 | Apter et al. |
| 2011/0022170 A1 | 1/2011 | Simpson et al. |
| 2011/0098811 A1 | 4/2011 | Hong et al. |
| 2011/0109874 A1 | 5/2011 | Piers et al. |
| 2011/0125261 A1 | 5/2011 | Portney |
| 2011/0149236 A1 | 6/2011 | Weeber |
| 2011/0166652 A1 | 7/2011 | Bogaert et al. |
| 2011/0267693 A1 | 11/2011 | Kobayashi et al. |
| 2011/0270596 A1 | 11/2011 | Weeber |
| 2011/0292335 A1* | 12/2011 | Schwiegerling ....... G02C 7/028 351/159.44 |
| 2011/0313522 A1 | 12/2011 | Hayes |
| 2011/0313523 A1 | 12/2011 | Hayes |
| 2011/0313525 A1 | 12/2011 | Cumming |
| 2011/0317124 A1 | 12/2011 | Weeber et al. |
| 2011/0317126 A1 | 12/2011 | Weeber |
| 2012/0029630 A1 | 2/2012 | Piers et al. |
| 2012/0059464 A1 | 3/2012 | Zhao |
| 2012/0140166 A1 | 6/2012 | Zhao |
| 2012/0143326 A1 | 6/2012 | Canovas et al. |
| 2012/0154740 A1 | 6/2012 | Bradley et al. |
| 2012/0165932 A1 | 6/2012 | Argal et al. |
| 2012/0170121 A1* | 7/2012 | Okada ................ G02B 27/4211 359/566 |
| 2012/0283825 A1 | 11/2012 | Houbrechts et al. |
| 2012/0320335 A1 | 12/2012 | Weeber et al. |
| 2012/0323321 A1 | 12/2012 | Simonov et al. |
| 2013/0035760 A1 | 2/2013 | Portney |
| 2013/0046381 A1 | 2/2013 | Zalevsky et al. |
| 2013/0060330 A1 | 3/2013 | Weeber et al. |
| 2013/0107202 A1 | 5/2013 | Liang |
| 2013/0201445 A1 | 8/2013 | Das et al. |
| 2014/0172088 A1 | 6/2014 | Carson et al. |
| 2015/0022775 A1 | 1/2015 | Ando et al. |
| 2015/0029460 A1 | 1/2015 | Bradley et al. |
| 2015/0094807 A1 | 4/2015 | Piers et al. |
| 2015/0359625 A1 | 12/2015 | Argal et al. |
| 2016/0216535 A1 | 7/2016 | Zhao |
| 2016/0220350 A1 | 8/2016 | Gerlach |
| 2016/0220352 A1 | 8/2016 | Choi et al. |
| 2016/0320633 A1 | 11/2016 | Weeber |
| 2016/0334640 A1 | 11/2016 | De Juan, Jr. et al. |
| 2016/0341978 A1 | 11/2016 | Schwiegerling |
| 2017/0172088 A1* | 6/2017 | May ........................ A01H 5/08 |
| 2017/0209259 A1 | 7/2017 | Choi et al. |
| 2017/0216020 A1 | 8/2017 | Weeber et al. |
| 2017/0219846 A1 | 8/2017 | Ando |
| 2017/0227789 A1 | 8/2017 | Ando et al. |
| 2017/0239038 A1 | 8/2017 | Choi et al. |
| 2017/0245985 A1 | 8/2017 | Canovas et al. |
| 2017/0245986 A1 | 8/2017 | Canovas et al. |
| 2017/0245987 A1 | 8/2017 | Canovas et al. |
| 2017/0252151 A1* | 9/2017 | Mackool .............. G02B 5/1895 |
| 2018/0092739 A1 | 4/2018 | Pagnoulle et al. |
| 2018/0132996 A1 | 5/2018 | Tiwari et al. |
| 2018/0147050 A1 | 5/2018 | Choi et al. |
| 2018/0147052 A1 | 5/2018 | Hong et al. |
| 2018/0275428 A1 | 9/2018 | Ando |
| 2018/0373060 A1 | 12/2018 | Knox et al. |
| 2019/0004335 A1 | 1/2019 | Weeber et al. |
| 2019/0224000 A1 | 7/2019 | Choi et al. |
| 2019/0254810 A1 | 8/2019 | Tiwari et al. |
| 2019/0307557 A1 | 10/2019 | De Carvalho et al. |
| 2019/0314148 A1 | 10/2019 | Liu |
| 2020/0038172 A1 | 2/2020 | Hussain et al. |

FOREIGN PATENT DOCUMENTS

| | | |
|---|---|---|
| CA | 2507659 A1 | 6/2004 |
| CA | 2590085 A1 | 6/2006 |
| CN | 1951340 A | 4/2007 |
| CN | 101181171 B | 4/2011 |
| CN | 102665611 A | 9/2012 |
| DE | 69715830 T2 | 8/2003 |
| EP | 335731 A2 | 10/1989 |
| EP | 342895 A2 | 11/1989 |
| EP | 0343067 A1 | 11/1989 |
| EP | 355230 A2 | 2/1990 |
| EP | 0369561 A2 | 5/1990 |
| EP | 375291 A2 | 6/1990 |
| EP | 412751 A2 | 2/1991 |
| EP | 0457553 A2 | 11/1991 |
| EP | 470811 A2 | 2/1992 |
| EP | 0537643 A1 | 4/1993 |
| EP | 605841 A1 | 7/1994 |
| EP | 0316162 B1 | 10/1995 |
| EP | 355230 B1 | 10/1995 |
| EP | 681198 A1 | 11/1995 |

(56) References Cited

FOREIGN PATENT DOCUMENTS

| | | |
|---|---|---|
| EP | 0537643 B1 | 3/1997 |
| EP | 0926531 A1 | 6/1999 |
| EP | 949529 A2 | 10/1999 |
| EP | 1376203 A2 | 1/2004 |
| EP | 1424049 A1 | 6/2004 |
| EP | 1862148 A1 | 12/2007 |
| EP | 1310267 B1 | 1/2008 |
| EP | 1891912 A1 | 2/2008 |
| EP | 2043558 A2 | 4/2009 |
| EP | 2045648 A1 | 4/2009 |
| EP | 1402308 B1 | 5/2009 |
| EP | 1424049 B1 | 6/2009 |
| EP | 2103279 A1 | 9/2009 |
| EP | 2113226 A1 | 11/2009 |
| EP | 2365379 A1 | 9/2011 |
| EP | 2377493 A1 | 10/2011 |
| EP | 2378319 A1 | 10/2011 |
| EP | 2290411 B1 | 5/2012 |
| EP | 2363097 B1 | 9/2012 |
| EP | 2812882 A1 | 12/2014 |
| EP | 2813881 A1 | 12/2014 |
| EP | 2349093 B1 | 10/2015 |
| EP | 3150170 B1 | 12/2017 |
| EP | 2527908 B1 | 3/2019 |
| IT | 1215851 B | 2/1990 |
| JP | 1154119 A | 6/1989 |
| JP | 2028615 A | 1/1990 |
| JP | 2079815 A | 3/1990 |
| JP | 2137814 A | 5/1990 |
| JP | 2249631 A | 10/1990 |
| JP | 3011315 A2 | 1/1991 |
| JP | 2000511299 A | 8/2000 |
| JP | 2003532157 A | 10/2003 |
| JP | 2010158315 A | 7/2010 |
| JP | 2013101323 A | 5/2013 |
| KR | 101154066 B1 | 6/2012 |
| RU | 2011154235 A | 7/2013 |
| RU | 2011154238 A | 7/2013 |
| WO | 9002963 A1 | 3/1990 |
| WO | 9222264 A1 | 12/1992 |
| WO | 9303409 A1 | 2/1993 |
| WO | 9413225 A1 | 6/1994 |
| WO | 9417435 A1 | 8/1994 |
| WO | 9724639 A1 | 7/1997 |
| WO | 9744689 A1 | 11/1997 |
| WO | 9831299 A2 | 7/1998 |
| WO | 9907309 A1 | 2/1999 |
| WO | 9923526 A1 | 5/1999 |
| WO | 0019906 A1 | 4/2000 |
| WO | 0076426 A2 | 12/2000 |
| WO | 0121061 A1 | 3/2001 |
| WO | 0163344 A1 | 8/2001 |
| WO | 0182839 A1 | 11/2001 |
| WO | 0189424 A1 | 11/2001 |
| WO | 0221194 A2 | 3/2002 |
| WO | 0234158 A2 | 5/2002 |
| WO | 02084381 A2 | 10/2002 |
| WO | 02088830 A1 | 11/2002 |
| WO | 03009053 A1 | 1/2003 |
| WO | 2004013680 A1 | 2/2004 |
| WO | 2004034129 A1 | 4/2004 |
| WO | 2004049979 A1 | 6/2004 |
| WO | 2004090611 A2 | 10/2004 |
| WO | 2004096014 A2 | 11/2004 |
| WO | 2004113959 A2 | 12/2004 |
| WO | 05019906 A1 | 3/2005 |
| WO | 06025726 A1 | 3/2006 |
| WO | 2006047698 A1 | 5/2006 |
| WO | 06060477 A2 | 6/2006 |
| WO | 2006060480 A2 | 6/2006 |
| WO | 2006067255 A1 | 6/2006 |
| WO | 2007092948 A1 | 8/2007 |
| WO | 2007133384 A2 | 11/2007 |
| WO | 2008045847 A2 | 4/2008 |
| WO | 2008150982 A1 | 12/2008 |
| WO | 2009017403 A1 | 2/2009 |
| WO | 2009027438 A2 | 3/2009 |
| WO | 2009043985 A1 | 4/2009 |
| WO | 2009058755 A1 | 5/2009 |
| WO | 2009076670 A1 | 6/2009 |
| WO | 2009130610 A2 | 10/2009 |
| WO | 2009148454 A1 | 12/2009 |
| WO | 2010046356 A1 | 4/2010 |
| WO | 2010054255 A1 | 5/2010 |
| WO | 2010059764 A1 | 5/2010 |
| WO | 2010079528 A1 | 7/2010 |
| WO | 2010093975 A2 | 8/2010 |
| WO | 2010100523 A1 | 9/2010 |
| WO | 2010104530 A1 | 9/2010 |
| WO | 2010144315 A1 | 12/2010 |
| WO | 2011024125 A1 | 3/2011 |
| WO | 2011055228 A2 | 5/2011 |
| WO | 2011075641 A2 | 6/2011 |
| WO | 2011075668 A1 | 6/2011 |
| WO | 2012004746 A2 | 1/2012 |
| WO | 2012031211 A1 | 3/2012 |
| WO | 2012070313 A1 | 5/2012 |
| WO | 2012078763 A1 | 6/2012 |
| WO | 2012085917 A1 | 6/2012 |
| WO | 2012122411 A1 | 9/2012 |
| WO | 2012140389 A1 | 10/2012 |
| WO | 2013018379 A1 | 2/2013 |
| WO | 2013028992 A1 | 2/2013 |
| WO | 2013093916 A1 | 6/2013 |
| WO | 2013114209 A2 | 8/2013 |
| WO | 2013116133 A1 | 8/2013 |
| WO | 2013118177 A1 | 8/2013 |
| WO | 2013118499 A1 | 8/2013 |
| WO | 2014008343 A1 | 1/2014 |
| WO | 2014033543 A2 | 3/2014 |
| WO | 2014091528 A1 | 6/2014 |
| WO | 2014111831 A1 | 7/2014 |
| WO | 2014189049 A1 | 11/2014 |
| WO | 2017137841 A1 | 8/2017 |
| WO | 2017149403 A1 | 9/2017 |
| WO | 2018093873 A1 | 5/2018 |
| WO | 2018150236 A1 | 8/2018 |
| WO | 2019130030 A1 | 7/2019 |
| WO | 2020115104 A1 | 6/2020 |

OTHER PUBLICATIONS

Alfonso J.F., et al., "Prospective Study of the Acri.LISA Bifocal Intraocular Lens," Journal of Cataract Refractive Surgery, Nov. 2007, vol. 33 (11), pp. 1930-1935.

Alvarez S. L. et al., "Spectral threshold: measurement and clinical applications," British Journal of Ophthalmology, 1983, 67, 504-507.

Apple D.J., et al., Eds., "Intraocular Lenses: Evolution, Designs, Complications and Pathology," in: New Concepts in Intraocular Lens Implantation, Williams & Wilkins publisher, Jan. 1989, vol. 22 (36), pp. 205-221.

Apple D.J., et al., Eds., "Intraocular Lenses: Evolution, Designs, Complications and Pathology," in: New Concepts in Intraocular Lens Implantation, Williams & Wilkins publisher, Jan. 1989, vol. 36 (1), pp. 21-36.

Artal P., et al., "Contributions of the Cornea and the Lens to the Aberrations of the Human Eye," Optics Letters, 1998, vol. 23 (21), pp. 1713-1715.

Atchinson D.A., "Design of Aspheric Intraocular Lens," Ophthalmic & Physiological Optics, 1991, vol. 11 (2), pp. 137-146.

Atchinson D.A., et al., "Optical Design of Intraocular Lenses II. Off-Axis performance," Optometry & Vision Science, 1989, vol. 66 (9), pp. 579-590.

Atchinson D.A., et al., "Third-Order Aberrations of Pseudophakic Eyes," Ophthalmic and Physiological Optics, 1989, vol. 9, pp. 205-211.

Atchinson D.A., "Optical Design of Intraocular Lenses. I. On-Axis Performance," American Academy of Optometry, 1989, vol. 66 (8), pp. 492-506.

Atchinson D.A., "Optical design of intraocular lenses III. On-Axis Performance in the Presence of Lens Displacement," American Academy of Optometry, 1989, vol. 66 (10), pp. 671-681.

(56) References Cited

OTHER PUBLICATIONS

Atchinson, "Refractive errors induced by displacement of intraocular lenses within the pseudophakic eye," Optometry & Vision Science, 1989, 66 (3), 146-152.
Bonnet R., et al., "New Method of Topographical Ophthalmometry-Its Theoretical and Clinical Applications," American Journal of Optometry, 1962, vol. 39 (5), pp. 227-251.
Bradley A. et al., "Achromatizing the Human Eye" Optometry & Vision Science, 1991, vol. 68 (8), pp. 608-616.
Buralli D.A., et al., "Optical Performance of Holographic Kinoforms," Applied Optics, Mar. 1989, vol. 28 (5), pp. 976-983.
Canovas C., et al., "Hybrid Adaptive—Optics Visual Simulator," Optical Letters, Jan. 15, 2010, vol. 35 (2), pp. 196-198.
Cohen A.L., "Diffractive Bifocal Lens Design," Optometry and Vision Science, Jun. 1993, vol. 70 (6), pp. 461-468.
Cohen A.L., "Practical Design of a Bifocal Hologram Contact Lens or Intraocular Lens," Applied Optics, Jul. 1, 1992, vol. 31 (19), pp. 3750-3754.
Diffractive Lenses for Extended Depth of Focus and Presbyopic Correction, Presentation from Wavefront Congress held on Feb. 15, 2008, Rochester, New York.
Doskolovich L.L., et al., "Special Diffractive Lenses," Lens and Optical Systems Design, Apr. 1992, vol. 1780, pp. 393-402.
Dwyer W. O. et al., "Racial Differences In Color Vision: Do They Exist", American Journal of Optometry & Physiological Optics, 1975, 52, 224-229.
El Hage S.G., et al., "Contribution of the Crystalline Lens to the Spherical Aberration of the Eye," 1973, vol. 63 (2), pp. 205-211.
Futhey J.A., "Diffractive Bifocal Intraocular Lens," SPIE, 1989, vol. 1052, pp. 142-148.
Geun Y., et al., "Visual Performance after Correcting the Monchromatic and Chromatic Aberrations of the Eye," Journal of the Optical Society of America, 2002, vol. 19 (2), pp. 266-275.
Glasser A. et al., "Presbyopia and the optical changes in the human crystalline lens with age," Vision Res, 1998, 38 (2), 209-229.
Greivenkamp J.E., et al., "Visual Acuity Modeling Using Optical Raytracing of Schematic Eyes," American Journal of Ophthalmology, 1995, vol. 120 (2), pp. 227-240.
Griswold Scott et al., "Scotopic Spectral Sensitivity of Phakic and Aphakic Observers Extending into the Near Ultraviolet," Vision res, 1992, 32 (9), 1739-1743.
Guirao A., et al., "Corneal Wave Aberration from Videokeratography: Accuracy and Limitations of the Procedure," Journal of the Optical Society of America, 2000, vol. 17 (6), pp. 955-965.
Iovs, 1999, 40 (4), S535.
Kiely et al., "The mean shape of the human cornea," Optica ACTA, 1982, 29 (8), 1027-1040.
Kokoschka S., et al., "Influence of Field Size on the Spectral Sensitivity of the Eye in the Photopic and Mesopic Range," American Journal of Optometry and Physiological Optics, 1985, vol. 62 (2), pp. 119-126.
Liang J., et al., "Objective Measurement of Wave Aberrations of The Human Eye With The Use of a Hartmann-Shack Wave-Front Sensor," Journal of the Optical Society of America, 1994, vol. 11 (7), pp. 1949-1957.
Lindsay R., et al., "Descriptors of Corneal Shape," Optometry and Vision Science, 1998, vol. 75 (2), pp. 156-158.
Liou H.L., et al., "Anatomically Accurate, Finite Model Eye for Optical Modeling," Journal of Optical Society of America, Aug. 1997, vol. 14 (8), pp. 1684-1695.
Lotmar, "Theoretical eye model with aspherics," Journal of the Optical Society of America, 1971, 61 (11), 1522-1529.
Malacara D., et al., "Wavefront Fitting With Discrete Orthogonal Polynomials In a Unit Radius Circle," Optical Engineering, 1990, vol. 29 (6), pp. 672-675.
Mandell R.B., et al., "Mathematical Model of the Corneal Contour," 1965, School of Optometry, University of California, Berkeley, pp. 183-197.

Marcos S., et al., "A New Approach to the Study of Ocular Chromatic Aberrations," Vision Research, 1999, vol. 39 (26), pp. 4309-4323.
Marsack J.D., et al., "Metrics of Optical Quality Derived from Wave Aberrations Predict Visual Performance," Journal of Vision, Apr. 2004, vol. 4 (4), pp. 322-328.
Monsoriu J.A., et al., "Devil's Lenses," Optics Express, Oct. 17, 2007, vol. 15 (21), pp. 13858-13864.
Mordi J.A., et al., "Influence of Age of Chromatic Aberration of the Human Eye," American Journal of Optometry & Physiological Optics, 1985, vol. 62 (12), pp. 864-869.
Navarro R., et al., "Accommodation-Dependent Model of the Human Eye with Aspherics," Journal of the Optical Society of America, Aug. 1985, vol. 2 (8), pp. 1273-1281.
Norrby S., et al., "Model Eyes for Evaluation of Intraocular Lenses," Applied Optics, Sep. 7, 2007, vol. 46 (26), pp. 6595-6605.
"Optical Design," Military Standardization Handbook, 1962, Chapter 4, U.S. Department of Defense MIL-HDBK-141, 4-1-4-19.
Oshika T., et al., "Changes in Corneal Wavefront Aberrations with Aging," Investigative Ophthalmology & Visual Science, 1999, vol. 40 (7), pp. 1351-1355.
Patel S., et al., "Shape and Radius of Posterior Corneal Surface," Refractive and Corneal Surgery, 1993, vol. 9 (3), pp. 173-181.
Piers P.A., et al., "Eye Models for the Prediction of Contrast Vision in Patients with New Intraocular Lens Designs," Optics Letters, Apr. 1, 2004, vol. 29 (7), pp. 733-735.
Piers P.A., et al., "Theoretical Comparison of Aberration-Correcting Customized and Aspheric Intraocular Lenses," Journal of Refractive Surgery, Apr. 2007, vol. 23 (4), pp. 374-384.
Said et al., "The Variation with Age of the Spectral Transmissivity of the Living Human Crystalline Lens," Gerontologia, 1959, 213-231.
Schwiegerling et al., "Representation of videokeratoscopic height data with Zemike polynomials," Journal of the Optical Society of America, 1995, 12 (10), 2105-2113.
Castignoles F., et al., "Comparison of the Efficiency, MTF and Chromatic Properties of Four Diffractive Bifocal Intraocular Lens Designs," Optics Express, Mar. 2010, vol. 18 (5), pp. 5245-5256.
Sokolowski M., et al. "Hybrid Heptafocal Intraocular Lenses," Optica Applicata, Dec. 2015, vol. 45 (3), pp. 285-298.
International Search Report and written opinion for Application No. PCT/EP2018/066780, dated Oct. 1, 2018, 14 pages.
Morlock, R., et al., "Patient-Reported Spectacle Independence Questionnaire (PRSIQ): Development and Validation," American Journal of Ophthalmology, Jun. 2017, vol. 178, pp. 101-114.
Seitz B., et al., "Corneal Topography," Current Opinion in Ophthalmolgy, 1997, vol. 8 (4), pp. 8-24.
Siedlecki D., et al., "Radial Gradient index Intraocular Lens: a Theoretical Model," Journal of Modern Optics, Feb. 20-Mar. 10, 2008, vol. 55 (4-5), pp. 639-647.
Smith G. et al., "The spherical aberration of the crystalline lens of the human eye," Vision Res., 2001, 41 (2), 235-243.
Smith Kinney, "Sensitivity of the eye to spectral radiation at scotopic and mesopic intensity levels," Journal of the Optical Society of America, 1955, 45 (7), 507-514.
Terwee T., et al., "Visualization of the Retinal Image in an Eye Model With Spherical and Aspheric, Diffractive, and Refractive Multifocal Intraocular Lenses," Journal of Refractive Surgery, Mar. 2008, vol. 24 (3), pp. 223-232.
Thibos L. N. et al., "The chromatic eye: a new reduced-eye model of ocular chromatic aberration in humans," Applied Optics, 1992, 31 (19), 3594-3600.
Thibos L. N. et al., "Theork and measurement of ocular chromatic aberration," Vision Res, 1988, 30 (1), 33-49.
Townsley, "New Knowledge of the corneal contour," Contacto, 1970, pp. 38-43.
Van Den Berg T.J., "Analysis of Intraocular Straylight, Especially in Relation to Age," Optometry and Vision Science, Feb. 1995, vol. 72 (2), pp. 52-59.
Van Meeteren A., "Calculations on the Optical Modulation Transfer Function of the Human Eye for White Light," Optica Acta, May 1974, vol. 21 (5), pp. 395-412.

(56) References Cited

OTHER PUBLICATIONS

Verriest G., "The Spectral Curve of Relative Luminous Efficiency in Different Age Groups of Aphakic Eyes," Mod Probl Ophthalmol., 1974, 13, 314-317.
Villegas E.A., et al., "Correlation between Optical and Psychophy, Sical Parameters as a Function of Defocus," Optometry and Vision Science, Jan. 1, 2002, vol. 79 (1), pp. 60-67.
Wang J.Y., et al., "Wave-Front Interpretation With Zemike Polynomials," Applied Optics, 1980, vol. 19 (9), pp. 1510-1518.
Guillon M., et al., "Corneal Topography: A Clinical Model," Ophthalmic & Physiological Optics, 1986, vol. 6 (1), pp. 47-56.
Smith G., et al., "The spherical aberration of intra-ocular lenses," Department of Optometry, 1988, vol. 8 (3), pp. 287-294.

\* cited by examiner

NON-REPEATING ECHELETTES AND RELATED INTRAOCULAR LENSES FOR PRESBYOPIA TREATMENT

CROSS-REFERENCE AND RELATED APPLICATIONS

This application claims priority to, and the benefit of, under U.S.C. § 119(e) of U.S. Provisional Appl. No. 62/527,720, filed on Jun. 30, 2017, which is incorporated herein by reference in its entirety.

BACKGROUND

Embodiments of the present invention relate to vision treatment techniques and in particular, to ophthalmic lenses such as, for example, contact lenses, corneal inlays or onlays, or intraocular lenses (IOLs) including, for example, phakic IOLs and piggyback IOLs (i.e. IOLs implanted in an eye already having an IOL).

Presbyopia is a condition that affects the accommodation properties of the eye. As objects move closer to a young, properly functioning eye, the effects of ciliary muscle contraction and zonular relaxation allow the lens of the eye to change shape, and thus increase its optical power and ability to focus at near distances. This accommodation can allow the eye to focus and refocus between near and far objects.

Presbyopia normally develops as a person ages, and is associated with a natural progressive loss of accommodation. The presbyopic eye often loses the ability to rapidly and easily refocus on objects at varying distances. The effects of presbyopia usually become noticeable after the age of 45 years. By the age of 65 years, the crystalline lens has often lost almost all elastic properties and has only a limited ability to change shape.

Along with reductions in accommodation of the eye, age may also induce clouding of the lens due to the formation of a cataract. A cataract may form in the hard central nucleus of the lens, in the softer peripheral cortical portion of the lens, or at the back of the lens. Cataracts can be treated by the replacement of the cloudy natural lens with an artificial lens. An artificial lens replaces the natural lens in the eye, with the artificial lens often being referred to as an intraocular lens or "IOL".

Monofocal IOLs are intended to provide vision correction at one distance only, usually the far focus. At the very least, since a monofocal IOL provides vision treatment at only one distance and since the typical correction is for far distance, spectacles are usually needed for good vision at near distances and sometimes for good vision at intermediate distances. The term "near vision" generally corresponds to vision provided when objects are at a distance from the subject eye at equal; or less than 1.5 feet. The term "distant vision" generally corresponds to vision provided when objects are at a distance of at least about 5-6 feet or greater. The term "intermediate vision" corresponds to vision provided when objects are at a distance of about 1.5 feet to about 5-6 feet from the subject eye. Such characterizations of near, intermediate, and far vision correspond to those addressed in Morlock R, Wirth R J, Tally S R, Garufis C, Heichel C W D, Patient-Reported Spectacle Independence Questionnaire (PRSIQ): Development and Validation. Am J Ophthalmology 2017; 178:101-114.

There have been various attempts to address limitations associated with monofocal IOLs. For example, multifocal IOLs have been proposed that deliver, in principle, two foci, one near and one far, optionally with some degree of intermediate focus. Such multifocal, or bifocal, IOLs are intended to provide good vision at two distances, and include both refractive and diffractive multifocal IOLs. In some instances, a multifocal IOL intended to correct vision at two distances may provide a near (add) power of about 3.0 or 4.0 diopters.

Multifocal IOLs may, for example, rely on a diffractive optical surface to direct portions of the light energy toward differing focal distances, thereby allowing the patient to clearly see both near and far objects. Multifocal ophthalmic lenses (including contact lenses or the like) have also been proposed for treatment of presbyopia without removal of the natural crystalline lens. Diffractive optical surfaces, either monofocal or multifocal, may also be configured to provide reduced chromatic aberration.

Diffractive monofocal and multifocal lenses can make use of a material having a given refractive index and a surface curvature which provide a refractive power. Diffractive lenses have a diffractive profile which confers the lens with a diffractive power that contributes to the overall optical power of the lens. The diffractive profile is typically characterized by a number of diffractive zones. When used for ophthalmic lenses these zones are typically annular lens zones, or echelettes, spaced about the optical axis of the lens. Each echelette may be defined by an optical zone, a transition zone between the optical zone and an optical zone of an adjacent echelette, and an echelette geometry. The echelette geometry includes an inner and outer diameter and a shape or slope of the optical zone, a height or step height, and a shape of the transition zone. The surface area or diameter of the echelettes largely determines the diffractive power(s) of the lens and the step height of the transition between echelettes largely determines the light distribution between the different powers. Together, these echelettes form a diffractive profile.

Diffractive multifocal lenses may have some form of apodization, e.g. as described in U.S. Pat. No. 5,699,142. Apodization is achieved by subsequently reducing the step height of the adjacent echelettes (bifocal), or adjacent sets of echelettes (trifocal or quadrifocal). The echelettes follow a general rule or equation, having the stepheight as the only variable. Therefore, this specific application is considered as a repeating structure.

A multifocal diffractive profile of the lens may be used to mitigate presbyopia by providing two or more optical powers; for example, one for near vision and one for far vision. The lenses may also take the form of an intraocular lens placed within the capsular bag of the eye, replacing the original lens, or placed in front of the natural crystalline lens. The lenses may also be in the form of a contact lens, most commonly a bifocal contact lens, or in any other form mentioned herein.

Although multifocal ophthalmic lenses lead to improved quality of vision for many patients, additional improvements would be beneficial. For example, some pseudophakic patients experience undesirable visual effects (dysphotopsia), e.g. glare or halos. Halos may arise when light from the unused focal image creates an out-of-focus image that is superimposed on the used focal image. For example, if light from a distant point source is imaged onto the retina by the distant focus of a bifocal IOL, the near focus of the IOL will simultaneously superimpose a defocused image on top of the image formed by the distant focus. This defocused image may manifest itself in the form of a ring of light surrounding the in-focus image, and is referred to as a halo. Another area of improvement revolves around the typical bifocality of multifocal lenses. While multifocal ophthalmic lenses typically provide adequate near and far vision, intermediate vision may be compromised.

A lens with an extended range of vision may thus provide certain patients the benefits of good vision at a range of distances, while having reduced or no dysphotopsia. Various techniques for extending the depth of focus of an IOL have been proposed. For example, some approaches are based on a bulls-eye refractive principle, and involve a central zone with a slightly increased power. Other techniques include an asphere or include refractive zones with different refractive zonal powers.

Although certain proposed treatments may provide some benefit to patients in need thereof, further advances would be desirable. For example, it would be desirable to provide improved IOL systems and methods that confer enhanced image quality across a wide and extended range of foci without dysphotopsia. Embodiments of the present invention provide solutions that address the problems described above, and hence provide answers to at least some of these outstanding needs.

BRIEF SUMMARY

Embodiments herein described include IOLs with a first surface and a second surface disposed about an optical axis, and a diffractive profile imposed on one of the first surface or the second surface. The diffractive profile consists of a plurality of echelettes arranged around the optical axis, having a profile in r-squared space. The echelettes may be non-repeating over the optical zone considered for vision.

Embodiments herein described include IOLs including an optic having a first surface and a second surface each disposed about an optical axis and extending radially outward from the optical axis to an outer periphery of the optic. The first surface faces opposite the second surface and joins to the second surface at the outer periphery of the optic. A diffractive profile is imposed on the first surface and includes a plurality of echelettes. At least one of the plurality of echelettes does not repeat on the first surface between the optical axis and the outer periphery of the optic.

Embodiments herein described include IOLs having an optical surface disposed about an optical axis, the optical surface including a central zone extending radially outward from the optical axis to a radial distance of 1.5 millimeters. A diffractive profile is imposed on the optical surface, and includes a plurality of echelettes disposed on the central zone. At least one of the plurality of echelettes does not repeat on the central zone. In one embodiment, the central zone may extend to a radial distance of 2.5 millimeters. In one embodiment, the central zone may extend outward from the optical axis to a radial distance of 0.5 millimeters from the outer periphery of the optic.

Embodiments herein described include IOLs including an optic having a first surface and a second surface each disposed about an optical axis and extending radially outward from the optical axis to an outer periphery of the optic. The first surface faces opposite the second surface and joins to the second surface at the outer periphery of the optic. A diffractive profile is imposed on the first surface and includes a plurality of echelettes. At least one of the plurality of echelettes has a profile in r-squared space that is different than a profile in r-squared space of any other echelette that is disposed on the first surface between the optical axis and the outer periphery of the optic.

Embodiments herein described include IOLs having an optical surface disposed about an optical axis, the optical surface including a central zone extending radially outward from the optical axis to a radial distance of 1.5 millimeters. A diffractive profile is imposed on the optical surface, and includes a plurality of echelettes disposed on the central zone. At least one of the plurality of echelettes on the central zone has a profile in r-squared space that is different than a profile in r-squared space of any other echelette that is on the central zone. In one embodiment, the central zone may extend to a radial distance of 2.5 millimeters. In one embodiment, the central zone may extend outward from the optical axis to a radial distance of 0.5 millimeters from the outer periphery of the optic.

Embodiments herein described include IOLs with a first surface and a second surface disposed about an optical axis, and a diffractive profile imposed on one of the first surface or the second surface. The diffractive profile may include a central zone, a peripheral zone, and an intermediate zone positioned between the central zone and the peripheral zone. At least one of the three zones may include a set of echelettes that is non-repeating.

Embodiments herein described include IOLs in which at least one echelette is not repeated in an adjacent echelette, and the at least one echelette is not part of a repeating set of at least two echelettes.

Embodiments herein described include IOLs with an optical surface disposed about an optical axis and a diffractive profile imposed on the optical surface, and including a plurality of echelettes. One of the plurality of echelettes is repeated on the optical surface, does not form part of a set of adjacent echelettes that repeats on the optical surface, and is not repeated in any adjacent echelette.

Embodiments herein described include IOLs with an optical surface disposed about an optical axis and a diffractive profile imposed on the optical surface, and including a plurality of echelettes. At least two adjacent echelettes of the plurality of echelettes form a set of echelettes. The set does not form part of a greater set of adjacent echelettes that repeats on the optical surface, is repeated on the optical surface to form one or more multiples of the set on the optical surface, and is separated from each of the one or more multiples of the set by at least one echelette.

Embodiments herein described also include manufacturing systems for making an ophthalmic lens. Such manufacturing system can include an input that accepts an ophthalmic lens prescription for a patient eye. A first module is configured to generate a diffractive profile based on the ophthalmic lens prescription. The diffractive profile includes a plurality of echelettes disposed on an optical surface. At least one of the plurality of echelettes does not repeat on the optical surface within an evaluation aperture. The manufacturing system includes a manufacturing assembly that fabricates the ophthalmic lens based on the diffractive profile.

Manufacturing system embodiments may include an input that accepts an ophthalmic lens prescription for a patient eye. A first module is configured to generate a diffractive profile based on the ophthalmic lens prescription. The diffractive profile includes a plurality of echelettes disposed on an optical surface. One of the plurality of echelettes is repeated on the optical surface, does not form part of a set of adjacent echelettes that repeats on the optical surface, and is not repeated in any adjacent echelette. The manufacturing system includes a manufacturing assembly that fabricates the ophthalmic lens based on the diffractive profile.

Manufacturing system embodiments may include an input that accepts an ophthalmic lens prescription for a patient eye. A first module is configured to generate a diffractive profile based on the ophthalmic lens prescription. The diffractive profile includes a plurality of echelettes disposed on an optical surface. At least two adjacent echelettes of the plurality of echelettes form a set of echelettes. The set does not form part of a greater set of adjacent echelettes that repeats on the optical surface, is repeated on the optical surface to form one or more multiples of the set on the optical surface, and is separated from each of the one or more multiples of the set by at least one echelette. The manufacturing system includes a manufacturing assembly that fabricates the ophthalmic lens based on the diffractive profile.

Embodiments herein described also include methods of designing an intraocular lens. Such methods can include defining an evaluation aperture for an optic and a diffractive profile and generating a diffractive lens surface based on the diffractive profile. The diffractive profile may include a plurality of echelettes disposed on an optical surface of the optic. At least one of the plurality of echelettes does not repeat on the optical surface within the evaluation aperture.

Embodiments herein described may also include methods of designing an intraocular lens. Such methods can include defining a diffractive profile and generating a diffractive lens surface based on the diffractive profile. The diffractive profile may include a plurality of echelettes disposed on an optical surface. One of the plurality of echelettes is repeated on the optical surface, does not form part of a set of adjacent echelettes that repeats on the optical surface, and is not repeated in any adjacent echelette.

Embodiments herein described may also include methods of designing an intraocular lens. Such methods can include defining a diffractive profile and generating a diffractive lens surface based on the diffractive profile. The diffractive profile may include a plurality of echelettes disposed on an optical surface. At least two adjacent echelettes of the plurality of echelettes form a set of echelettes. The set does not form part of a greater set of adjacent echelettes that repeats on the optical surface, is repeated on the optical surface to form one or more multiples of the set on the optical surface, and is separated from each of the one or more multiples of the set by at least one echelette.

DETAILED DESCRIPTION

Contemporary Lens Shapes and Diffractive Profiles

FIGS. 1A, 1B, 2A, 2B, 3A and 3B illustrate multifocal IOL lens geometries, aspects of which are described in U.S. Patent Publication No. 2011-0149236 A1, which is hereby incorporated by reference in its entirety.

Figure 1A:
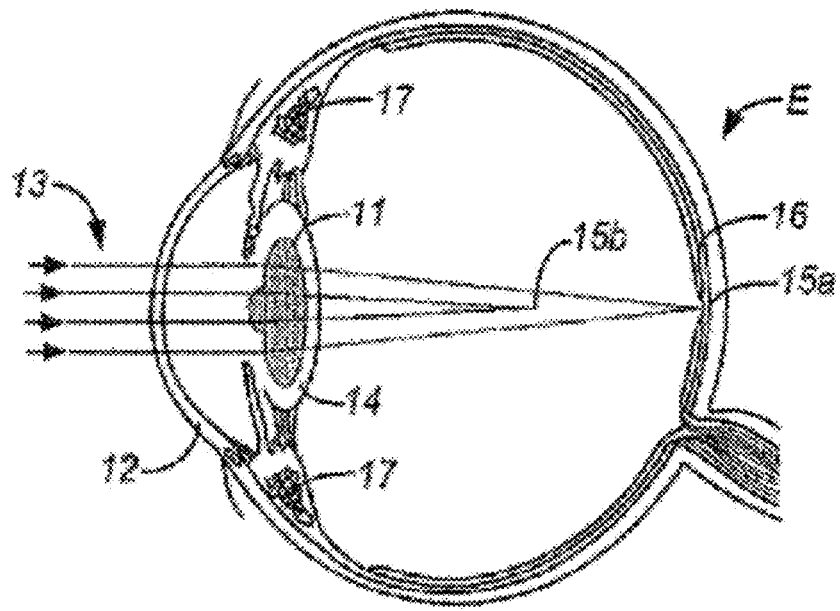
FIG. 1A illustrates a cross-sectional view of an eye with an implanted multifocal refractive intraocular lens.

FIG. 1A is a cross-sectional view of an eye E fit with a multifocal IOL 11. As shown, multifocal IOL 11 may, for example, comprise a bifocal IOL. Multifocal IOL 11 receives light from at least a portion of cornea 12 at the front of eye E and is generally centered about the optical axis of eye E. For ease of reference and clarity, FIGS. 1A and 1B do not disclose the refractive properties of other parts of the eye, such as the corneal surfaces. Only the refractive and/or diffractive properties of the multifocal IOL 11 are illustrated.

Each major face of lens 11, including the anterior (front) surface and posterior (back) surface, generally has a refractive profile, e.g. biconvex, plano-convex, plano-concave, meniscus, etc. The two surfaces together, in relation to the properties of the surrounding aqueous humor, cornea, and other optical components of the overall optical system, define the effects of the lens 11 on the imaging performance by eye E. Conventional, monofocal IOLs have a refractive power based on the refractive index of the material from which the lens is made, and also on the curvature or shape of the front and rear surfaces or faces of the lens. One or more support elements may be configured to secure the lens 11 to a patient's eye.

Multifocal lenses may optionally also make special use of the refractive properties of the lens. Such lenses generally include different powers in different regions of the lens so as to mitigate the effects of presbyopia. For example, as shown in FIG. 1A, a perimeter region of refractive multifocal lens 11 may have a power which is suitable for viewing at far viewing distances. The same refractive multifocal lens 11 may also include an inner region having a higher surface curvature and a generally higher overall power (sometimes referred to as a positive add power) suitable for viewing at near distances.

Figure 1B:
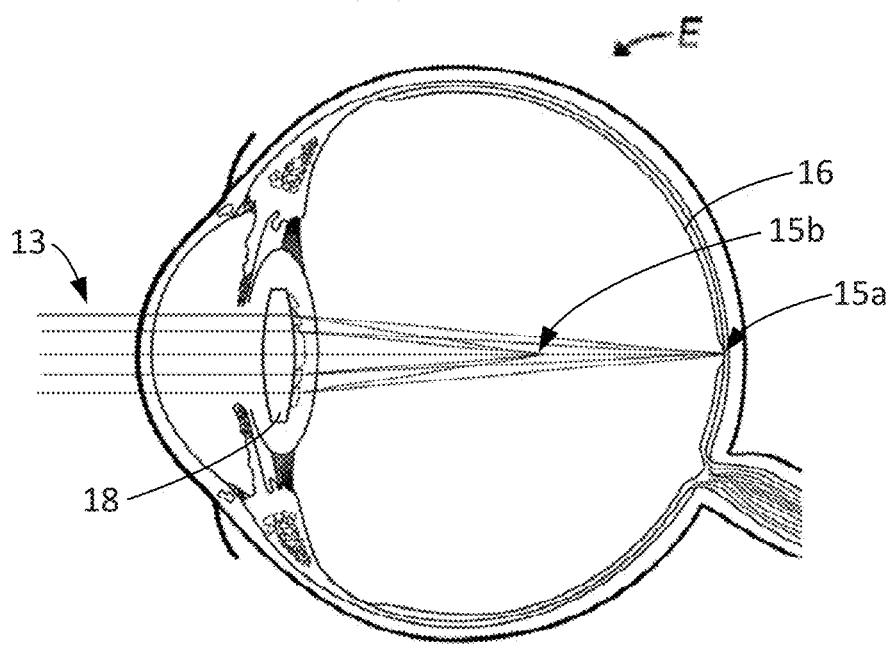
FIG. 1B illustrates a cross-sectional view of an eye having an implanted multifocal diffractive intraocular lens.

Rather than relying entirely on the refractive properties of the lens, multifocal diffractive IOLs or contact lenses can also have a diffractive power, as illustrated by the IOL 18 shown in FIG. 1B. The diffractive power can, for example, comprise positive or negative power, and that diffractive power may be a significant (or even the primary) contributor to the overall optical power of the lens. The diffractive power is conferred by a plurality of concentric diffractive zones which form a diffractive profile. The diffractive profile may either be imposed on the anterior face or posterior face or both.

The diffractive profile of a diffractive multifocal lens directs incoming light into a number of diffraction orders. As light 13 enters from the front of the eye, the multifocal lens 18 directs light 13 to form a far field focus 15a on retina 16 for viewing distant objects and a near field focus 15b for viewing objects close to the eye. Depending on the distance from the source of light 13, the focus on retina 16 may be the near field focus 15b instead. Typically, far field focus 15a is associated with $0^{th}$ diffractive order and near field focus 15b is associated with the $1^{st}$ diffractive order, although other orders may be used as well.

Bifocal ophthalmic lens 18 typically distributes the majority of light energy into two viewing orders, often with the goal of splitting imaging light energy about evenly (50%: 50%), one viewing order corresponding to far vision and one viewing order corresponding to near vision, although typically, some fraction goes to non-viewing orders.

Corrective optics may be provided by phakic IOLs, which can be used to treat patients while leaving the natural lens in place. Phakic IOLs may be angle supported, iris supported, or sulcus supported. The phakic IOL can be placed over the natural crystalline lens or piggy-backed over another IOL. It is also envisioned that the present disclosure may be applied to inlays, onlays, accommodating IOLs, pseudophakic IOLs, other forms of intraocular implants, spectacles, and even laser vision correction.

Figure 2A:
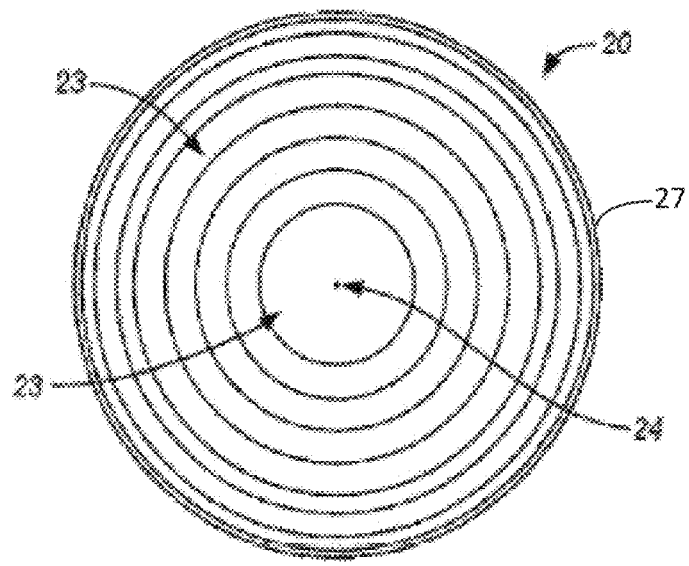
FIG. 2A illustrates a front view of a diffractive multifocal intraocular lens.
Figure 2B:
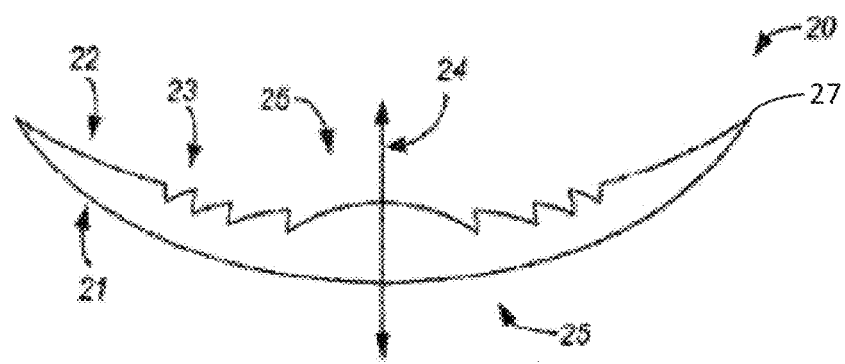
FIG. 2B illustrates a cross-sectional view of a diffractive multifocal intraocular lens.

FIGS. 2A and 2B show aspects of a conventional diffractive multifocal lens 20. Multifocal lens 20 may have certain optical properties that are generally similar to those of multifocal IOLs 11, 18 described above. Multifocal lens 20 comprises an optic with an anterior lens face 21 and a posterior lens face 22 disposed about optical axis 24. The faces 21, 22, or optical surfaces, extend radially outward from the optical axis 24 to an outer periphery 27 of the optic. The faces 21, 22 of lens 20 face opposite each other, and typically define a clear aperture 25. As used herein, the term "clear aperture" means the opening of a lens or optic that restricts the extent of a bundle of light rays from a distant source that can be imaged or focused by the lens or optic. The clear aperture is usually circular and is specified by its diameter, and is sometimes equal to the full diameter of the optic.

An evaluation aperture is defined as the aperture at which the performance of the lens is of particular interest. An example of such aperture is an aperture diameter of 3.0 mm. A 3.0 mm pupil diameter is representative for a "medium size" pupil under normal photopic light conditions (Watson A B, Yellott J I. A unified formula for light-adapted pupil size. J Vis 2012; 12:12, 1-16). A 3.0 mm physical pupil is also a standard pupil size for evaluation of IOLs in the ISO standard for IOLs (ISO 11979-2). Another aperture size of special interest is 5.0 mm. A 5.0 mm aperture represents a large pupil, e.g. representing the pupil size under mesopic or scotopic light conditions. A 5.0 mm physical pupil is also a standard pupil size for evaluation of IOLs in the ISO standard for IOLs (ISO 11979-2). Alternatively, an evaluation aperture may consist of an annulus having an inner radius and an outer radius. In other embodiments, alternative sizes of evaluation apertures may be utilized as desired. In one embodiment, the evaluation aperture may extend radially outward from the optical axis to 0.5 millimeters from the outer periphery of the optic.

When fitted onto the eye of a subject or patient, the optical axis of lens 20 is generally aligned with the optical axis of eye E. The curvature of lens 20 gives lens 20 an anterior refractive profile and a posterior refractive profile. Although a diffractive profile may also be imposed on either anterior face 21 and posterior face 22 or both, FIG. 2B shows posterior face 22 with a diffractive profile. The diffractive profile is characterized by a plurality of annular diffractive zones or echelettes 23 spaced about optical axis 24. The diffractive profile extends on the posterior optical surface between the optical axis 24 and the outer periphery 27 of the optic. While analytical optics theory generally assumes an infinite number of echelettes, a standard multifocal diffractive IOL typically has at least 9 echelettes, and may have over 30 echelettes. For the sake of clarity, FIG. 2B shows only 4 echelettes. Typically, an IOL is biconvex, or possibly plano-convex, or convex-concave, although an IOL could be plano-plano, or other refractive surface combinations.

Figure 3A:
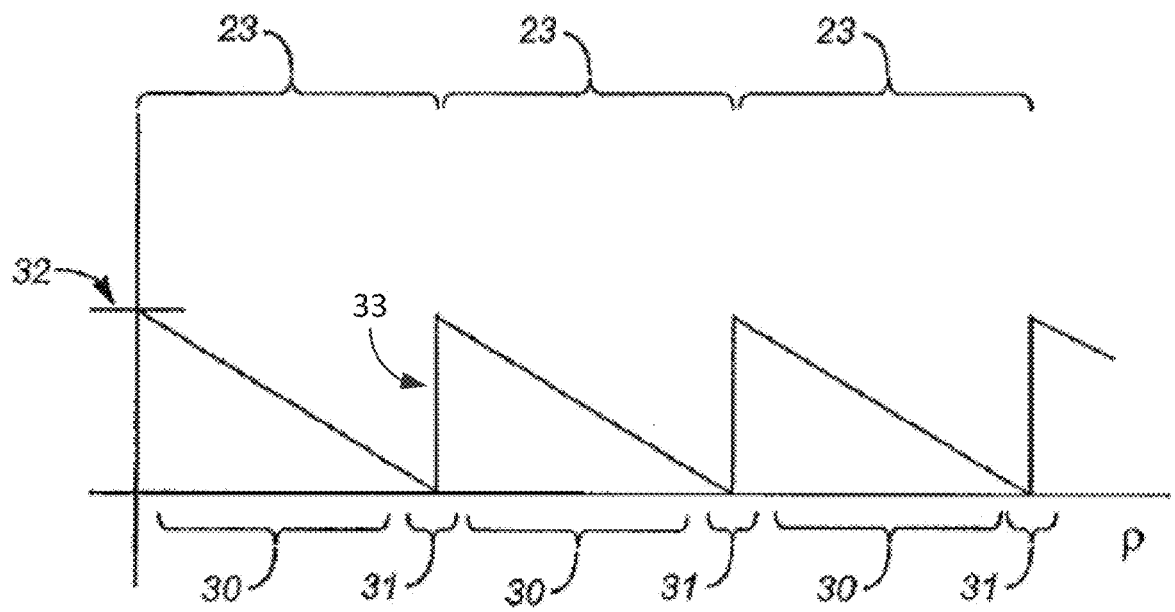
FIGS. 3A-3B are graphical representations of a portion of the diffractive profile of a conventional diffractive multifocal lens.
Figure 3B:
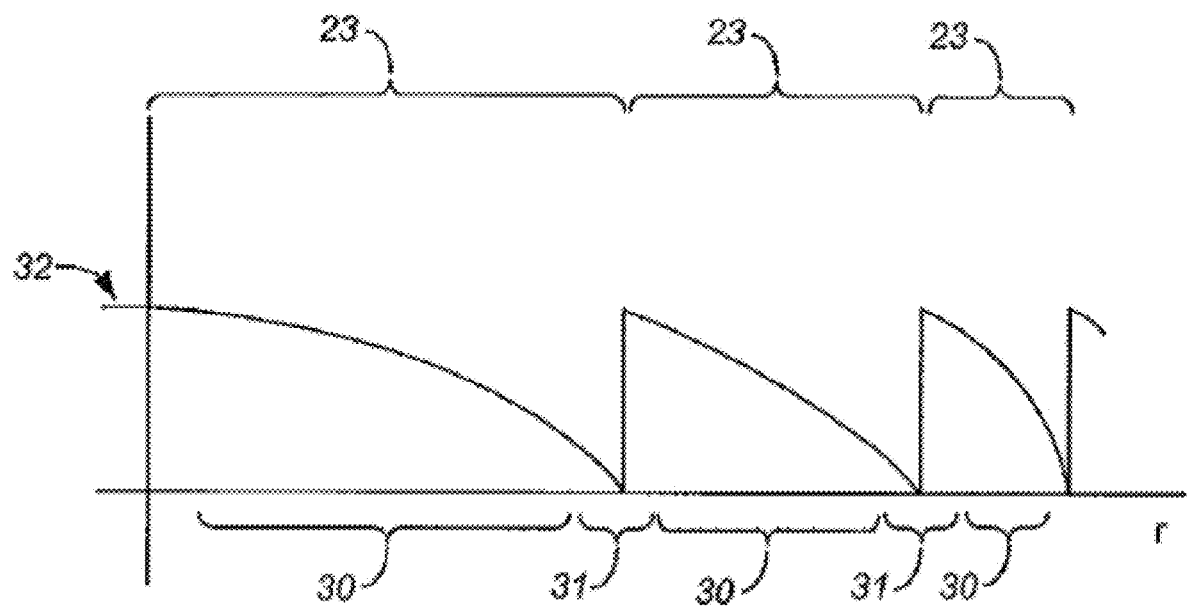

FIGS. 3A and 3B are graphical representations of a portion of a typical diffractive profile of a multifocal lens. While the graph shows only 3 echelettes, typical diffractive lenses extend to at least 9 echelettes to over 32 echelettes. In FIG. 3A, the height of the surface relief profile (from a plane perpendicular to the light rays) of each point on the echelette surface is plotted against the square of the radial distance ($r^2$ or $\rho$) from the optical axis of the lens (referred to as r-squared space). In multifocal lenses, each echelette 23 may have a diameter or distance from the optical axis which is often proportional to $\sqrt{n}$, n being the number of the echelette 23 as counted from optical axis 24. Each echelette has a characteristic optical zone 30 and transition zone 31. Optical zone 30 typically has a shape or downward slope that is parabolic as shown in FIG. 3B. The slope of each echelette in r-squared space (shown in FIG. 3A), however, is the same. As for the typical diffractive multifocal lens, as shown here, all echelettes have the same surface area. The area of echelettes 23 determines the diffractive power of lens 20, and, as area and radii are correlated, the diffractive power is also related to the radii of the echellettes. The physical offset of the trailing edge of each echelette to the leading edge of the adjacent echelette is the step height. An exemplary step height between adjacent echelettes is marked as reference number 33 in FIG. 3A. The step heights remain the same in r-squared space (FIG. 3A) and in linear space (FIG. 3B). The step offset is the height offset of the transition zone from the underlying base curve. An exemplary step offset is marked as reference number 414 in FIG. 4.

Figure 4:
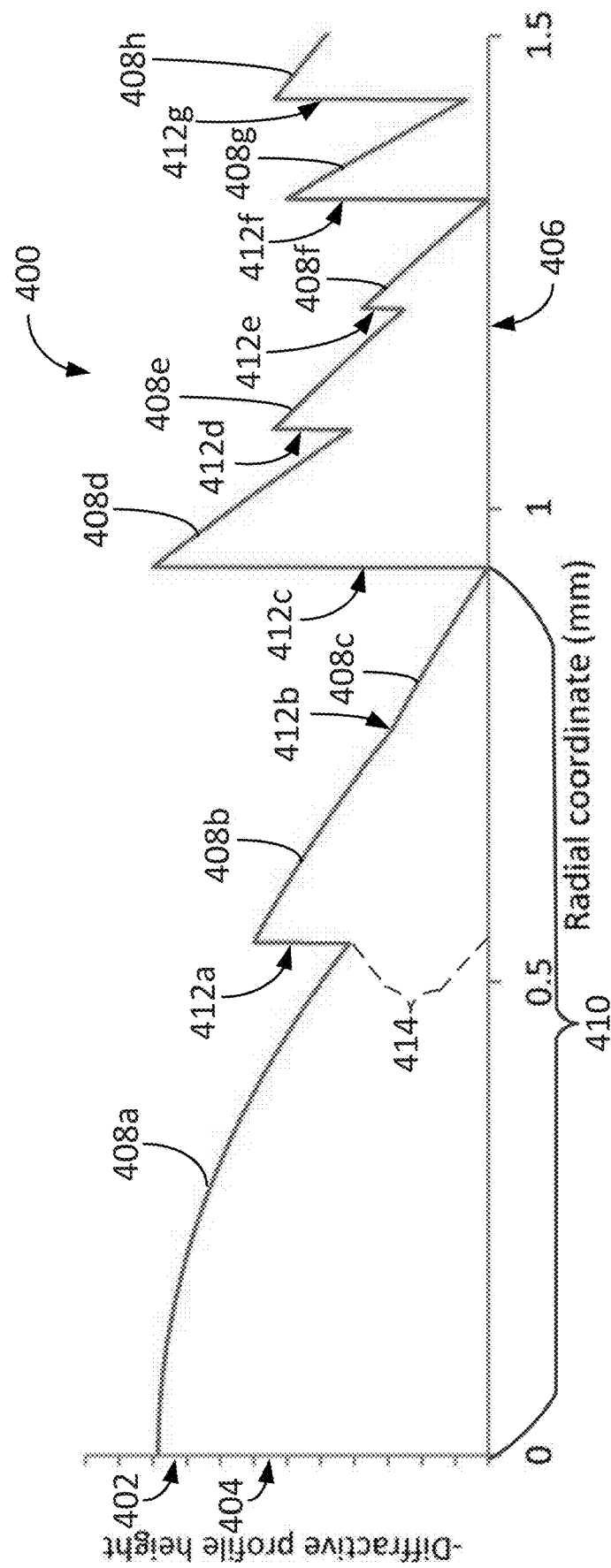
FIG. 4 is a graphical representation illustrating a lens profile for a diffractive lens according to certain embodiments of this disclosure.

FIG. 4 shows a graphical representation illustrating an embodiment of a diffractive profile 400. The diffractive profile 400 may result in a lens having an extended range of vision or a multifocal lens.

The diffractive profile 400, in the form of a sag profile, is shown extending outward from an optical axis 402. The diffractive zones, or echelettes, are shown extending radially outward from the optical axis 402, and would be arranged around the optical axis 402 (the other half of the diffractive profile 400 is not shown). The diffractive profile 400 is shown relative to the Y axis 404, which represents the height or phase shift of the diffractive profile 400. The height is shown in units of micrometers (each hash mark corresponding to one micrometer), and may represent the distance from the base curve of the lens. In other embodiments, other units or scalings may be utilized.

The height or phase shift of the diffractive profile 400 is shown in relation to the radius on the X axis 406 from the optical axis 402. The radius is shown in units of millimeters, although in other embodiments, other units or scalings may be utilized. The diffractive profile 400 may extend outward from the optical axis 402 for an evaluation radius of 1.5 millimeters (corresponding to an evaluation aperture of 3.0 millimeters), although in other embodiments the diffractive profile 400 may extend for a lesser or greater radius. The evaluation aperture may be considered to be a central zone of the optic, extending radially outward from the optical axis 402 to a distance (e.g., 1.5 millimeters). Each of the echelettes 408a-h shown in FIG. 4 do not repeat over the entire evaluation radius (and accordingly do not repeat over the entire evaluation aperture). Within the scope of this disclosure, at least one of the echelettes 408a-h may not repeat over the evaluation aperture, or at least two or at least three of the echelettes 408a-h may not repeat over the evaluation aperture, or any number of echelettes may not repeat over the evaluation aperture, up to the total number of echelettes 408a-h within the evaluation aperture. In one embodiment, the configuration of one or more non-repeating echelettes may extend to the entire surface of the optic upon which the diffractive profile 400 is disposed, which may be a greater distance then the evaluation aperture. In one embodiment, the configuration of one or more non-repeating echelettes may extend to the entire optical zone of the lens upon which the diffractive profile 400 is disposed.

In addition, the echelettes may be considered to form sets of echelettes, such as the set 410 shown in FIG. 4 corresponding to echelettes 408a-c. The set 410 is non-repeating over the evaluation radius (and accordingly non-repeating over the evaluation aperture). Within the scope of this disclosure, at least one of the sets of echelettes may not repeat over the evaluation aperture, or at least two or at least three of the sets of echelettes may not repeat over the evaluation aperture, or any number of sets of echelettes may not repeat over the evaluation aperture, up to the total number of sets of echelettes within the evaluation aperture. In one embodiment, this configuration of one or more non-repeating sets of echelettes may extend to the entire surface of the optic upon which the diffractive profile is disposed. In one embodiment, the configuration of one or more non-repeating sets of echelettes may extend to the entire optical zone of the lens upon which the diffractive profile 400 is disposed. The set 410 as shown in FIG. 4 includes three echelettes, although in other embodiments the non-repeating sets may include lesser or greater numbers of echelettes (e.g., at least two echelettes). At least one zone (e.g., a central zone, intermediate zone, peripheral zone) of the optical surface of the optic may include a set of echelettes that is non-repeating.

The echelettes 408a-h are each separated from an adjacent echellete by a respective transition zone 412a-g. Each echelette 408a-h has a profile defined by the shape or slope of the respective echelettes and the step height and step offsets (as discussed previously) at the respective adjacent transition zones (at the leading and trailing edge of each echelette). Each of the echelettes 408a-h shown in FIG. 4 has a different profile than the other echelettes on the evaluation aperture both in linear space and in r-squared space (discussed previously). Notably, transition zone 412b has a zero step height, which may serve to reduce stray light or halos that may otherwise be produced by a non-zero step height at a transition zone. One or more of the transition zones of a diffractive profile discussed herein may comprise a zero step height transition zone.

Figure 5:
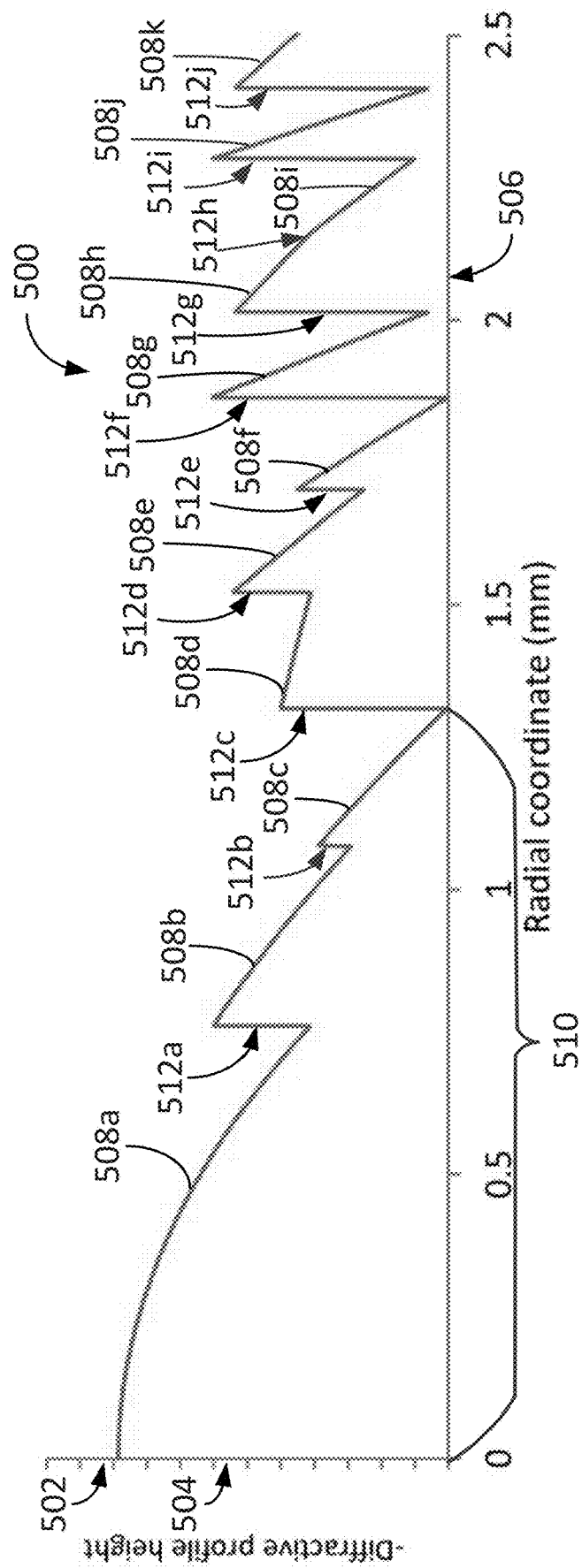
FIG. 5 is a graphical representation illustrating a lens profile for a diffractive lens according to certain embodiments of this disclosure.

The size and shape of the evaluation aperture may be varied as desired. For instance, FIG. 5 illustrates a larger evaluation radius of 2.5 millimeters (corresponding to an evaluation aperture of 5.0 millimeters). The evaluation aperture may be considered to be a central zone of the optic, extending radially outward from the optical axis 502 to a distance (e.g., 2.5 millimeters). The diffractive profile 500 is shown relative to the Y axis 504, which represents the height or phase shift of the diffractive profile 500. The height is shown in units of micrometers (each hash mark corresponding to one micrometer), and may represent the distance from the base curve of the lens. In other embodiments, other units or scalings may be utilized. The height or phase shift of the diffractive profile 500 is shown in relation to the radius on the X axis 506 from the optical axis 502.

Each of the echelettes 508a-k shown in FIG. 5 do not repeat over the entire evaluation radius (and accordingly do not repeat over the entire evaluation aperture). Similar to the embodiment discussed in regard to FIG. 4, within the scope of this disclosure, at least one or more of the echelettes may not repeat over the evaluation aperture.

In addition, similar to the embodiment shown in FIG. 4, the echelettes may be considered to form sets of echelettes, such as the set 510 shown in FIG. 5 corresponding to echelettes 508a-c. The set 510 is non-repeating over the evaluation radius (and accordingly the evaluation aperture). Similar to the embodiment discussed in regard to FIG. 4, within the scope of this disclosure, at least one or more of the sets of echelettes may not repeat over the evaluation aperture.

The echelettes 508a-k are each separated from an adjacent echellete by a respective transition zone 512a-j. Each of the echelettes 508a-k shown in FIG. 5 has a different profile than the other echelettes on the evaluation aperture both in linear space and in r-squared space (discussed previously).

In both embodiments of FIG. 4 and FIG. 5, the optic, the clear optic, and the optical design, and the diffractive profile may extend outside of the evaluation aperture shown in the respective figures.

Within the scope of this disclosure, in embodiments, at least one echelette may repeat within the evaluation radius (and accordingly within the evaluation aperture). In addition, in embodiments, at least one echelette may repeat outside of the evaluation radius (and accordingly outside of the evaluation aperture).

Figure 6:
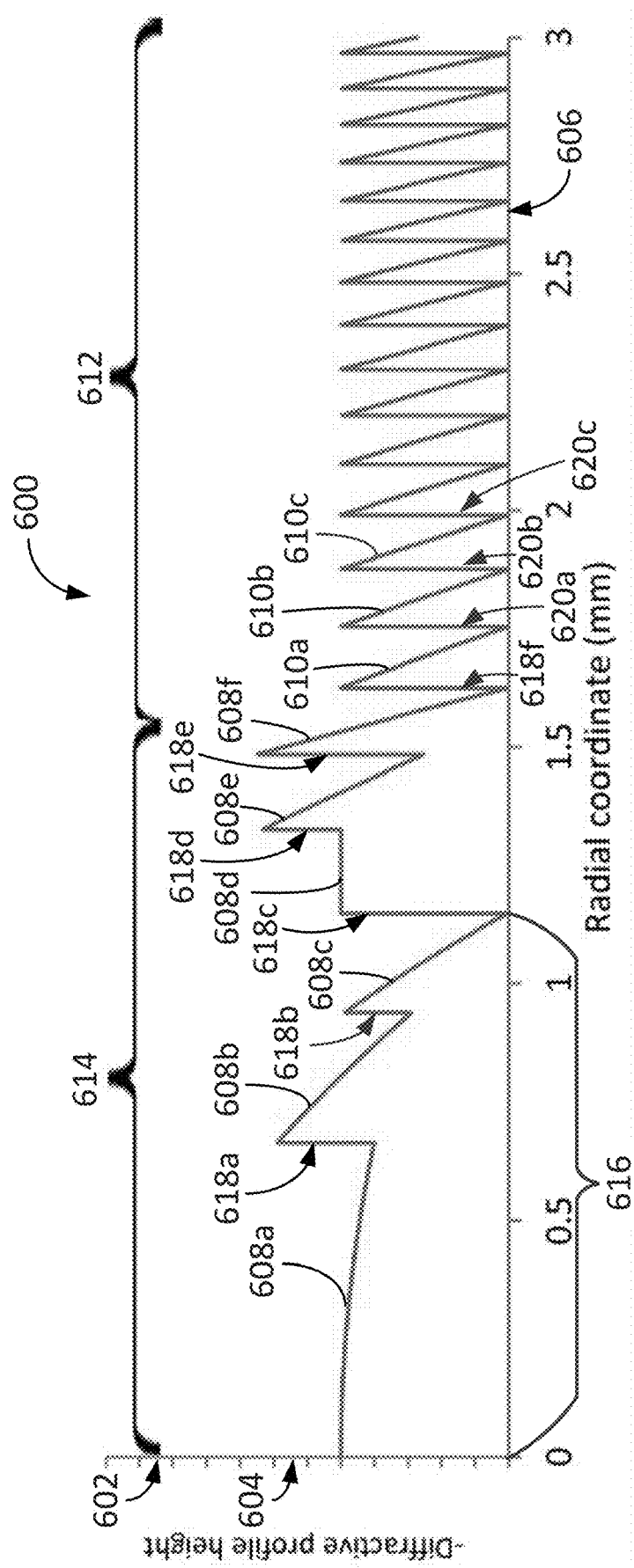
FIG. 6 is a graphical representation illustrating a lens profile for a diffractive lens according to certain embodiments of this disclosure.

FIG. 6 illustrates a diffractive profile 600 in which echelettes are repeating outside of the evaluation aperture. FIG. 6 illustrates an evaluation radius of 1.6 millimeters (corresponding to an evaluation aperture of 3.2 millimeters). The evaluation aperture extends radially outward from the optical axis 602 to a distance. The evaluation aperture may be considered to be a central zone of the optic. The diffractive profile 600 is shown relative to the Y axis 604, which represents the height or phase shift of the diffractive profile 600. The height is shown in units of micrometers (each hash mark corresponding to one micrometer), and may represent the distance from the base curve of the lens. In other embodiments, other units or scalings may be utilized. The height or phase shift of the diffractive profile 600 is shown in relation to the radius on the X axis 606 from the optical axis 602.

In this embodiment, each of the echelettes 608a-f within the evaluation radius do not repeat over the evaluation radius (and accordingly do not repeat over the entire evaluation aperture). Similar to the embodiments discussed in regard to FIGS. 4 and 5, within the scope of this disclosure, at least one or more of the echelettes 608a-f may not repeat over the evaluation aperture. However, the echelettes 610a-c outside the evaluation radius do repeat. The echelettes 610a-c repeat outward to a radial distance of about 3 millimeters (three echelettes 610a-c are marked in FIG. 6, however, fifteen total repeating echelettes 610a-c are shown in FIG. 6). The echlettes repeat on a zone 612 that is radially outward of the central zone 614. The zone 612 may be considered a peripheral zone, and the echelettes 610*a-c* may repeat entirely across the peripheral zone. In other embodiments, a lesser or greater number of repeating echelettes 610*a-c* may be provided. In one embodiment, at least one repeating echelette may be provided within the evaluation aperture. In one embodiment, at least one non-repeating echelette may be provided outside the evaluation aperture.

In addition, similar to the embodiment shown in FIGS. 4 and 5, the echelettes 608*a-f* may be considered to form sets of echlettes, such as the set 616 shown in FIG. 6 corresponding to echelettes 608*a-c*. The set 610 is non-repeating over the evaluation radius (and accordingly over the evaluation aperture). Similar to the embodiment discussed in regard to FIGS. 4 and 5, within the scope of this disclosure, at least one or more sets of echelettes may not repeat over the evaluation aperture.

The echelettes 608*a-f* are each separated from an adjacent echellete by a respective transition zone 618*a-f*. Each of the echelettes 608*a-f* has a different profile than the other echelettes 608*a-f* on the evaluation aperture both in linear space and in r-squared space (discussed previously). The echelettes 610*a-c* are also each separated from an adjacent echellete by a respective transition zone 620*a-c* and 618*f*. Each of the echelettes 610*a-c* shown in FIG. 6 has a same profile as the other echelettes on the zone 612 in r-squared space (discussed previously).

Figure 7:
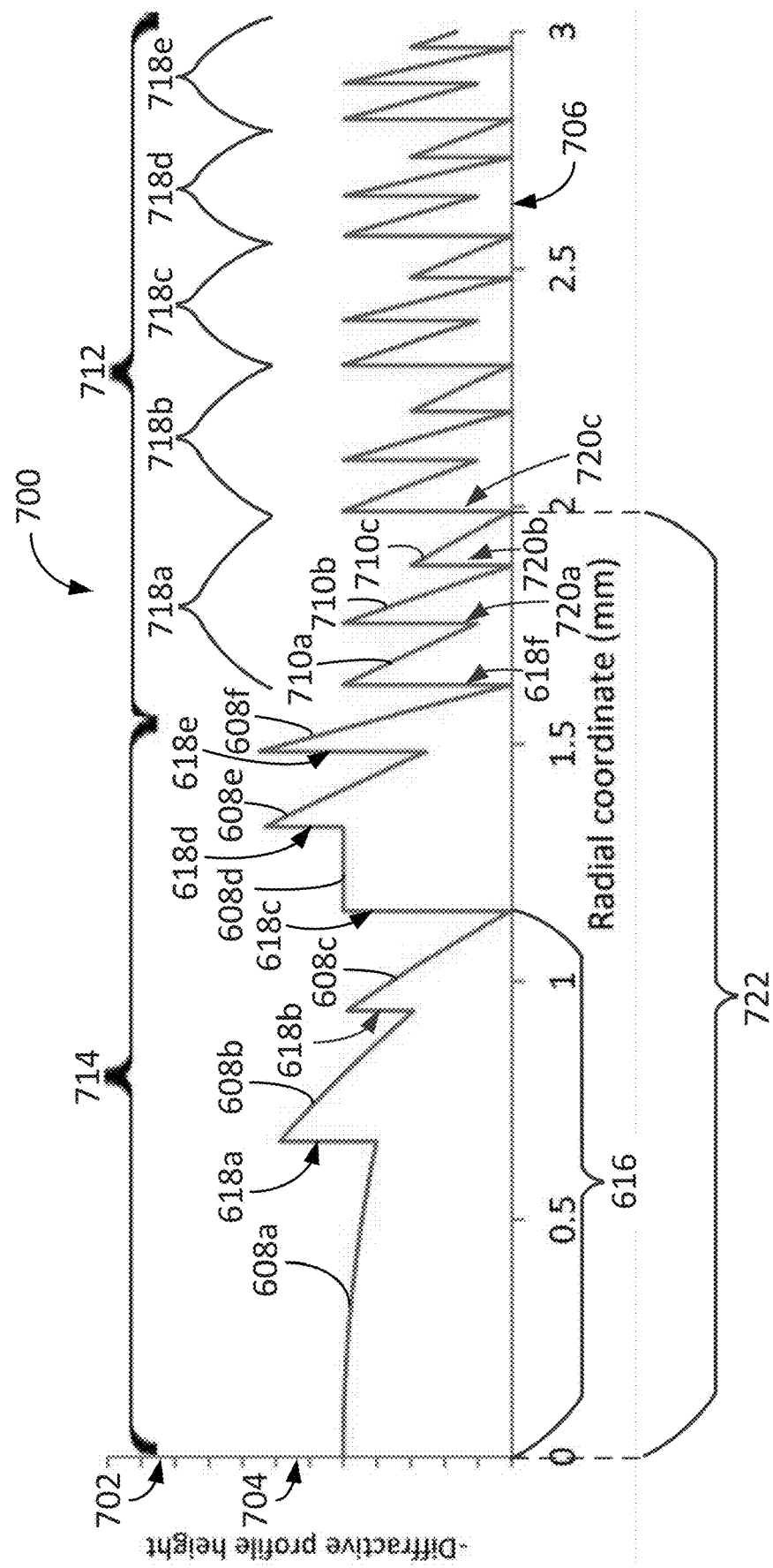
FIG. 7 is a graphical representation illustrating a lens profile for a diffractive lens according to certain embodiments of this disclosure.

FIG. 7 illustrates a diffractive profile 700 in which sets of echelettes are repeating outside of the evaluation aperture. FIG. 7 illustrates an evaluation radius of 1.6 millimeters (corresponding to an evaluation aperture of 3.2 millimeters). The evaluation aperture extends radially outward from the optical axis 702 to a distance. The evaluation aperture may be considered to be a central zone of the optic. The diffractive profile 700 is shown relative to the Y axis 704, which represents the height or phase shift of the diffractive profile 700. The height is shown in units of micrometers (each hash mark corresponding to one micrometer), and may represent the distance from the base curve of the lens. In other embodiments, other units or scalings may be utilized. The height or phase shift of the diffractive profile 700 is shown in relation to the radius on the X axis 706 from the optical axis 702.

FIG. 7 illustrates a variation on the diffractive profile shown in FIG. 6, in which the echelettes within the central zone 714 have the same profile as shown within the central zone 614 of FIG. 6. The echelettes 710*a-c* outside of the evaluation aperture (or central zone 714), however, form a set 718*a* of echelettes 710*a-c* that repeats on the entirety of the peripheral zone 712 outside of the evaluation aperture. The set 718*a* may repeat as sets 718*b-e* on the peripheral zone 712. The set 718*a* accordingly is repeated on the optical surface to form four multiples 718*b-e* of the set 718*a* on the optical surface. The sets 718*a-e* accordingly comprise a repeated set. The sets 718*a-e* are adjacent to each other. The sets 718*a* and 718*b* are not separated from each other by at least one echelette. In other embodiments, the set 718*a* may be repeated in a number of multiples that covers a lesser or greater portion of the peripheral zone 712. The set 718*a* shown in FIG. 7 includes three echelettes, although in other embodiments a greater or lesser number of echelettes may be utilized in the set (e.g., at least two echelettes in a set).

In one embodiment, a repeating set may be provided on the central zone 714.

The echelettes 710*a-c* are also each separated from an adjacent echellete by a respective transition zone 720*a-c* and 618*f*. Each of the sets 718*a-e* shown in FIG. 7 has a same profile as the other sets 718*a-e* on the zone 712 in r-squared space (discussed previously).

Alternatively, FIG. 7 may include an evaluation radius of 1.9 millimeters (marked with reference number 722), within which echelettes are non-repeating. However, the last three echelettes within the evaluation radius of 1.9 mm are repeated outside of the evaluation aperture.

Figure 8:
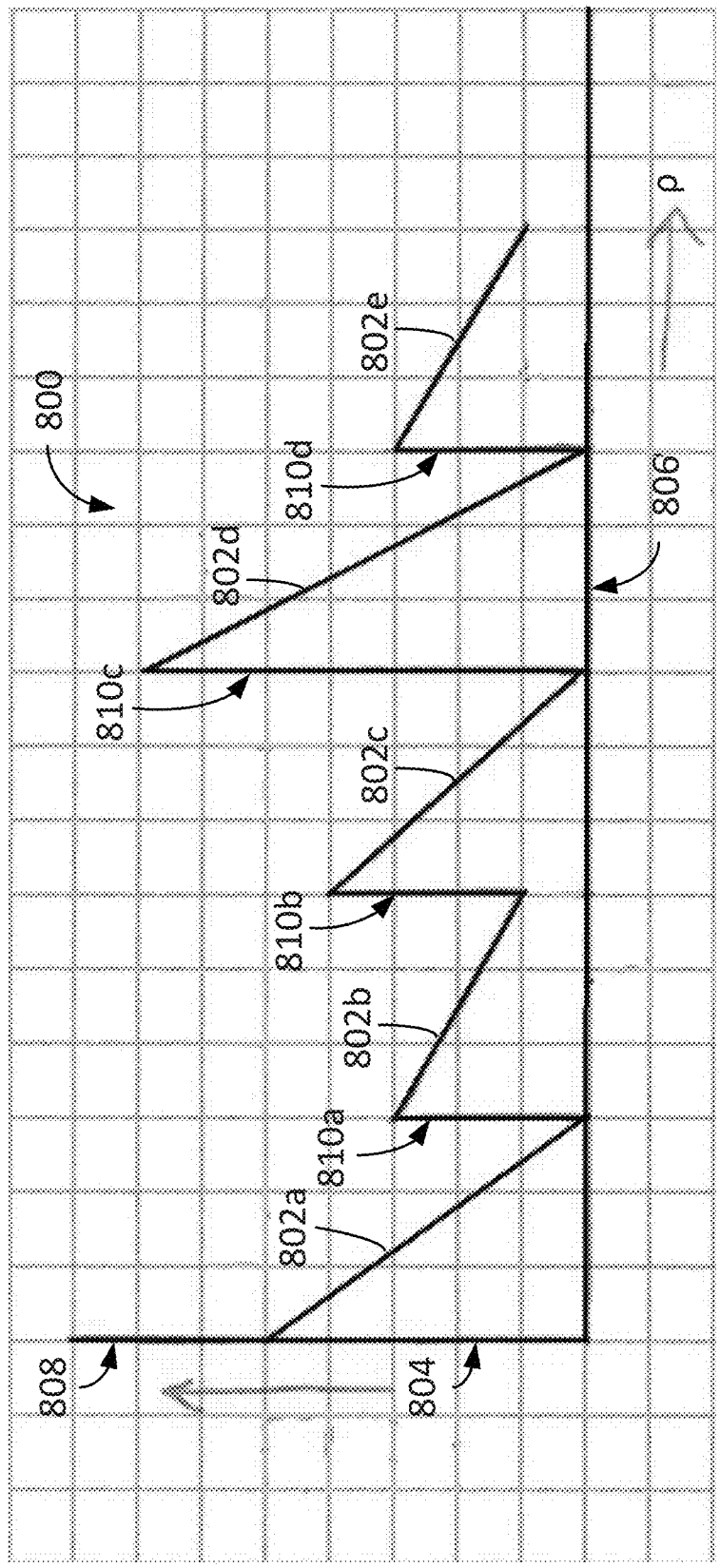
FIG. 8 is a graphical representation illustrating a lens profile for a diffractive lens according to certain embodiments of this disclosure.

FIG. 8 illustrates a diffractive profile 800 in which at least one of the echelettes 802*b* is repeated on the surface of the optic upon which it is disposed. The echelette 802*b* is repeated as echelette 802*e*. However, the echelette 802*b* is not adjacent the echelette 802*e*. Rather the echelette 802*b* is adjacent echelettes 802*a* and 802*c*, neither of which comprises a repetition of echelette 802*b*.

The diffractive profile 800 is shown relative to the Y axis 804, which represents the height or phase shift of the diffractive profile 800. The height is shown as a relative scaling of the heights of the echelettes 802*a-e*, and may represent the relative distance from the base curve of the lens. In other embodiments, other units or scalings may be utilized. The height or phase shift of the diffractive profile 800 is shown in relation to the square of the radial distance ($r^2$ or $\rho$), on the X axis 806, from the optical axis 808 (r-squared space).

The echelette 802*b* is not repeated in adjacent echelettes 802*a*, 802*c*. Echelette 802*e* is also not repeated in any adjacent echelette 802*d*. Echelette 802*b* and its repeated, or multiple, echelette 802*e* are separated by two echelettes 802*c*, 802*d*.

The echelette 802*b* does not form part of a set of adjacent echelettes that repeats on the optical surface upon which it is disposed. A set of adjacent echlettes would include two or more adjacent echelettes. For example, echelette 802*b* in combination with adjacent echelette 802*a* does not form a set of echelettes that repeats on the optical surface. Echelette 802*b* in combination with adjacent echelette 802*c* does not form a set of echelettes that repeats on the optical surface. A combination of echelette 802*b* with both echelettes 802*a* and 802*c*, or also with echelettes 802*d* and 802*e*, also do not form a set of echelettes that repeats on the optical surface. Accordingly, repeated echelette 802*b* does not form part of a set of adjacent echelettes that repeats on the optical surface upon which it is disposed. In contrast, echelette 710*c* shown in FIG. 7 repeats on the optical surface upon which it is disposed, and it forms part of a set 718*a* of adjacent echelettes that repeats on the optical surface (as sets 718*b*, 718*c*, 718*d*, 718*e*).

The echelettes 802*a-e* are each separated from an adjacent echellete by a respective transition zone 810*a-d*. Each of the echelettes 802*a-d* has a different profile than each of the other echelettes 802*a-d* both in linear space and in r-squared space (discussed previously). The echelettes 802*b* and 802*e*, however, have a same profile in r-squared space, as is visible in FIG. 8.

The echelette 802*b* may be repeated once on the optical surface upon which it is disposed, as shown in FIG. 8, to form the multiple echelette 802*e*. In other embodiments, the echelette 802*b* may be repeated on the optical surface at least twice. In one embodiment, one or more echeletes may repeat on the optical surface, without being repeated in any adjacent echelette, and not forming part of a set of adjacent echelettes that repeats on the optical surface.

The diffractive profile 800 includes three echelettes 802*a*, 802*c*, 802*d*, that do not repeat on the optical surface. In other embodiments, a greater or lesser number of echelettes that do not repeat on the optical surface may be provided (at least one non-repeating echelette). In one embodiment, echelettes that do repeat on the optical surface adjacent to each other may be provided. In one embodiment, one or more repeating sets of at least two echelettes may be provided, and the sets may be adjacent to each other.

In certain embodiments, the diffractive profile 800, or the configuration of echelettes discussed in regard to FIG. 8, may only extend over an evaluation radius (and accordingly an evaluation aperture). The evaluation radius may be sized and shaped as desired, and may have a size corresponding to a radius that is disclosed or discussed herein. In other embodiments, the diffractive profile 800, or the configuration of echelettes discussed in regard to FIG. 8, may extend to the entire surface of the optic upon which the diffractive profile is disposed, which may be a greater distance then the evaluation aperture. In one embodiment, the diffractive profile 800, or the configuration of echelettes discussed in regard to FIG. 8, may extend to the entire optical zone of the lens upon which the corresponding diffractive profile is disposed.

Figure 9:
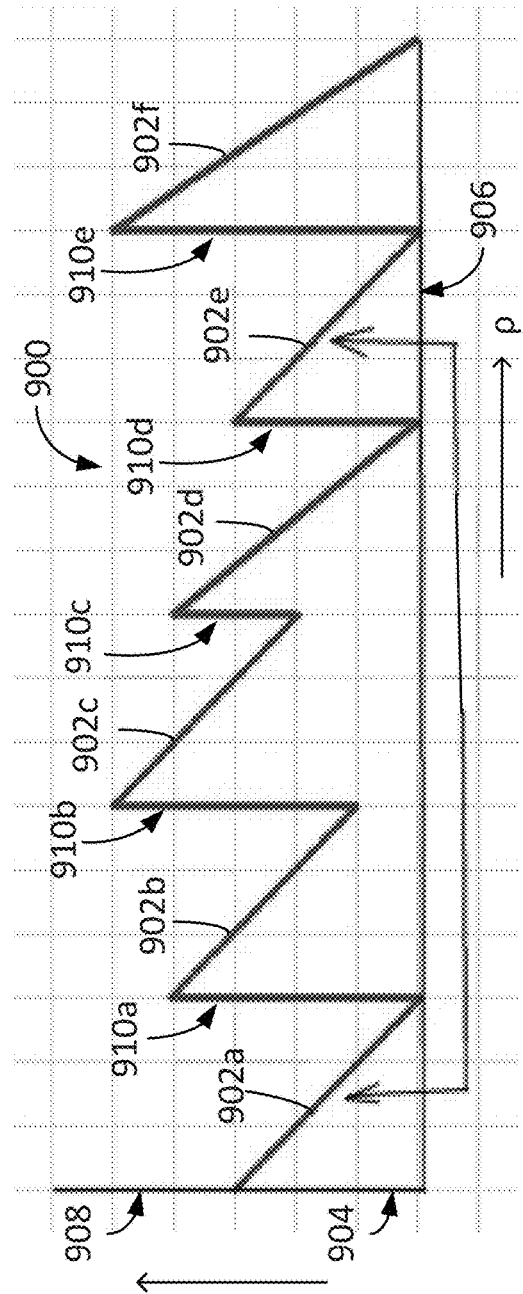
FIG. 9 is a graphical representation illustrating a lens profile for a diffractive lens according to certain embodiments of this disclosure.

FIG. 9 illustrates a diffractive profile 900 in which at least one of the echelettes 902a is repeated on the surface of the optic upon which it is disposed. The echelette 902a is repeated as echelette 902e (as indicated by the double arrow line pointing to the echelettes 902a, 902e). However, the echelette 902a is not adjacent the echelette 902e. Rather the echelette 902a is adjacent echelette 902b, which does not comprise a repetition of echelette 902a.

The diffractive profile 900 is shown relative to the Y axis 904, which represents the height or phase shift of the diffractive profile 900. The height is shown as a relative scaling of the heights of the echelettes 902a-f, and may represent the relative distance from the base curve of the lens. In other embodiments, other units or scalings may be utilized. The height or phase shift of the diffractive profile 900 is shown in relation to the square of the radial distance ($r^2$ or $\rho$), on the X axis 906, from the optical axis 908 (r-squared space).

The echelette 902a is not repeated in adjacent echelette 902b. Echelette 902e is also not repeated in any adjacent echelette 902d, 902f. Echelette 902a and its repeated, or multiple, echelette 902e are separated by three echelettes 902b-d.

As discussed in regard to the embodiment of FIG. 8, the echelette 902a does not form part of a set of adjacent echelettes that repeats on the optical surface upon which it is disposed. Similarly, the echelette 902e does not form part of a set of adjacent echelettes that repeats on the optical surface upon which it is disposed.

The echelettes 902a-f are each separated from an adjacent echellete by a respective transition zone 910a-e. Each of the echelettes 902b-d and 902f, has a different profile than each of the other echelettes 902a-f both in linear space and in r-squared space (discussed previously). The echelettes 902a and 902e, however, have a same profile in r-squared space, as is visible in FIG. 9.

The configuration of echelettes shown in FIG. 9 may be modified in any manner discussed in regard to the embodiment of FIG. 8.

Figure 10:
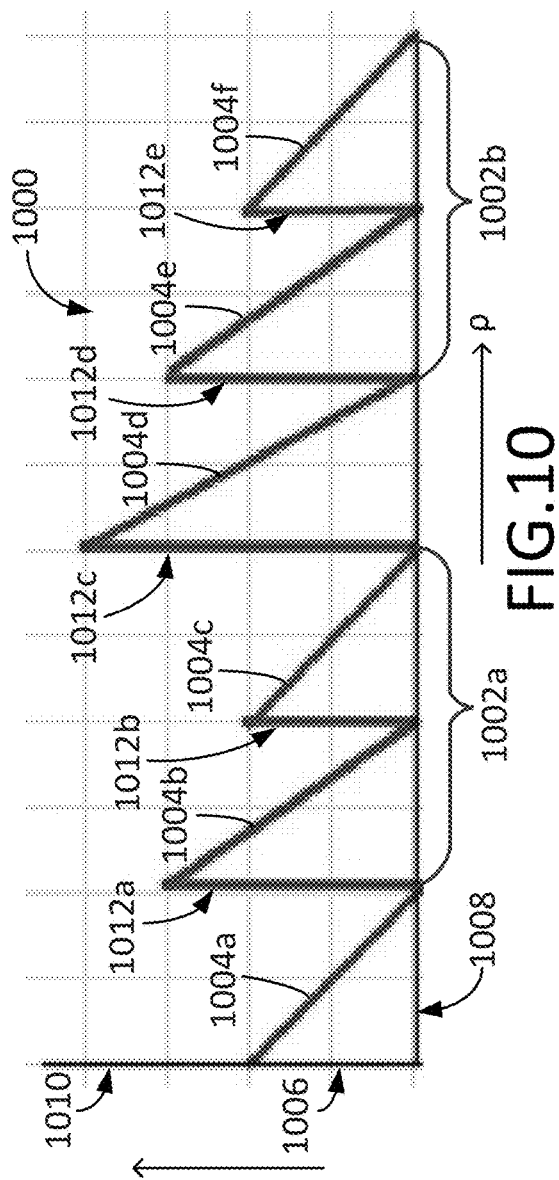
FIG. 10 is a graphical representation illustrating a lens profile for a diffractive lens according to certain embodiments of this disclosure.

FIG. 10 illustrates a diffractive profile 1000 in which at least one set 1002a of echelettes 1004b, 1004c is repeated on the surface of the optic upon which it is disposed. The set 1002a is repeated as the multiple set 1002b of echelettes 1004e, 1004f. However, the set 1002a is not adjacent the set 1002b. Rather the set 1002a is separated from the multiple set 1002b by at least one echelette 1004d. Echelette 1004d does not form part of either set 1002a or set 1002b.

The diffractive profile 1000 is shown relative to the Y axis 1006, which represents the height or phase shift of the diffractive profile 1000. The height is shown as a relative scaling of the heights of the echelettes 1004a-f, and may represent the relative distance from the base curve of the lens. In other embodiments, other units or scalings may be utilized. The height or phase shift of the diffractive profile 1000 is shown in relation to the square of the radial distance ($r^2$ or $\rho$), on the X axis 1008, from the optical axis 1010 (r-squared space).

The set 1002a is not repeated in adjacent echelettes 1004a, 1004d, or in any adjacent set of echelettes. The set 1002b is not repeated in adjacent echelette 1004d, and is also not repeated in any adjacent set of echelettes.

The set 1002a of echelettes 1004b, 1004c does not form part of greater set of adjacent echelettes that repeats on the optical surface. A greater set of adjacent echelettes would comprise a set of adjacent echelettes with a greater number of echelettes than set 1002a, and that also includes set 1002a. For example, set 1002a includes two adjacent echelettes 1004b and 1004c, and a greater set of adjacent echelettes would then include one or more additional adjacent echelettes (totaling a set with three or more adjacent echelettes). Notably, set 1002a is adjacent echelette 1004a. Set 1002a in combination with adjacent echelette 1004a does not form a greater set of adjacent echelettes that repeats on the optical surface. Set 1002a is adjacent echelette 1004d. Set 1002a in combination with adjacent echelette 1004d does not form a greater set of adjacent echelettes that repeats on the optical surface. A combination of set 1002a with both echelettes 1004a and 1004d, or also with echelettes 1004e and 1004f, also do not form a greater set of adjacent echelettes that repeats on the optical surface. In contrast, the embodiment shown in FIG. 7 displays a set of echelettes (710a and 710b) that forms part of a greater set 718a of adjacent echelettes (710a, 710b, and 710c) that repeats on the optical surface as multiple sets 718b, 718c, 718d and 718e.

The set 1002a shown in FIG. 10 includes two echelettes. In other embodiments, a set having properties discussed in regard to set 1002a may include two or more, or at least two, adjacent echelettes.

The set 1002a shown in FIG. 10 is repeated on the optical surface once to form a multiple set 1002b on the optical surface. In other embodiments, a set having properties discussed in regard to set 1002a may be repeated on the optical surface to form one or more multiples of the set, or at least one multiple of the set. The set may be separated from each of the one or more multiples of the set by at least one echelette, such that the set is not adjacent any of the multiples of the set.

The set 1002a shown in FIG. 10 is separated from the multiple set 1002b by one echelette 1004d. In other embodiments, a set having properties discussed in regard to set 1002a may be separated from each of the one or more multiples of the set by one or more, or at least one echelette.

The echelettes 1004a-f are each separated from an adjacent echellete by a respective transition zone 1012a-e. Each of the echelettes 1004a, 1004d, 1004f has a different profile than each of the other echelettes 1004a-f both in linear space and in r-squared space (discussed previously). The echelettes 1004b and 1004e have the same profile in r-squared space, as is visible in FIG. 10. The echelettes 1004c and 1004f have the same profile in r-squared space, as is visible in FIG. 10. The sets 1002a and 1002b of echlettes have the same profile in r-squared space, as is visible in FIG. 10.

In one embodiment, one or more sets of at least two adjacent echelettes may repeat on the optical surface to form one or more multiples of the respective set on the optical surface, each without forming part of a greater set of adjacent echelettes that repeats on the optical surface, and each being separated from each of the one or more multiples of the respective set by at least one echelette.

The diffractive profile 1000 includes two echelettes 1004a, 1004d, that do not repeat on the optical surface. In other embodiments, a greater or lesser number of echelettes that do not repeat on the optical surface may be provided (at least one non-repeating echelette). In one embodiment, echelettes that do repeat on the optical surface adjacent to each other may be provided. In one embodiment, one or more repeating sets of at least two echelettes may be provided, and the sets may be adjacent to each other.

In certain embodiments, the diffractive profile 1000, or the configuration of echelettes discussed in regard to FIG. 10, may only extend over an evaluation radius (and accordingly an evaluation aperture). The evaluation radius may be sized and shaped as desired, and may have a size corresponding to a radius that is disclosed herein. In other embodiments, the diffractive profile 1000, or the configuration of echelettes discussed in regard to FIG. 10, may extend to the entire surface of the optic upon which the diffractive profile is disposed, which may be a greater distance then the evaluation aperture. In one embodiment, the diffractive profile 1000, or the configuration of echelettes discussed in regard to FIG. 10, may extend to the entire optical zone of the lens upon which the corresponding diffractive profile is disposed.

Referring now to the embodiments disclosed in this application (and not solely to the embodiments of FIG. 10), the diffractive powers of the lens may vary, depending on the desired performance of the design. Diffractive powers up to 2.75-4.5D are intended for a design that provides adequate visual performance over the entire range of vision from far to intermediate distances and near. Lower diffractive powers may be beneficial if the desired performance is to emphasize good far and intermediate vision, while vision at near distances may be slightly reduced. Such lens design may have diffractive powers up to about 1.5-2.75D.

The diffractive profiles disclosed herein may result in a diffractive profile producing an extended range of vision for the patient.

In one embodiment, a diffractive profile may be positioned on a surface of a lens that is opposite an aspheric surface. The aspheric surface on the opposite side of the lens may be designed to reduce corneal spherical aberration of the patient.

In one embodiment, one or both surface may be aspherical, or include a refractive surface designed to extend the depth of focus, or create multifocality.

In one embodiment, a refractive zone on one or both surfaces, that may the same size or different in size as one of the diffractive zones. The refractive zone includes a refractive surface designed to extend the depth of focus, or create multifocality.

Any of the embodiments of lens profiles discussed herein may be apodized to produce a desired result. The apodization may result in the step heights and step offsets of the echelettes and the sets being varied according to the apodization. The apodized echelettes and the sets however, are still considered to be repeating over the optic of the lens.

The size and shape of the evaluation aperture may be varied as desired. In one embodiment, the evaluation aperture may extend to the entire optical zone of the lens. In one embodiment, the evaluation aperture may comprise an annulus disposed about the optical axis.

Figure 11:
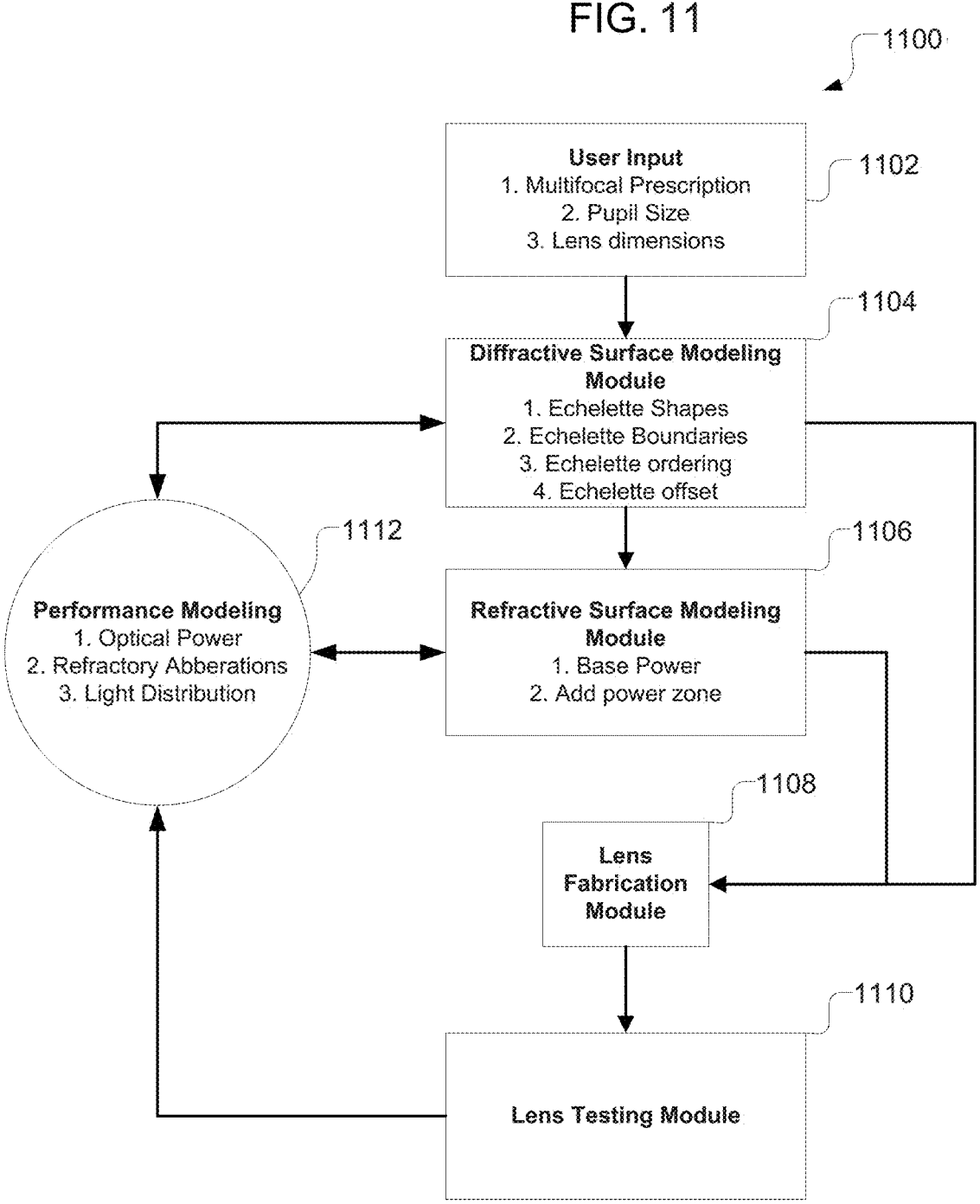
FIG. 11 is a simplified block diagram illustrating a system for generating a diffractive lens surface, in accordance with embodiments.

Systems and Methods for Determining Lens Shape:

FIG. 11 is a simplified block diagram illustrating a system 1100 for generating an ophthalmic lens based on a user input. The system 1100 may be used to generate any embodiment of lens disclosed or discussed in this application.

The system 1100 includes a user input module 1102 configured to receive user input defining aspects of the user and of a lens. The user input may also comprise a size and shape of a desired evaluation aperture. Aspects of a lens may include a diffractive lens prescription, which may comprise a multifocal lens prescription, anatomical dimensions like a pupil size performance, and lens dimensions, among other attributes. A lens prescription can include, for example, a preferred optical power or optical power profile for correcting far vision and an optical power or optical power profile for near vision. In some cases, a lens prescription can further include an optical power or optical power profile for correcting intermediate vision at two, or in some cases more than two intermediate foci, which may fall between the optical powers or ranges of optical powers described above. A pupil size performance can include a pupil radius of a patient and the visual field to be optimized. These parameters can also be related to patient's life style or profession, so that the design incorporates patient's visual needs as a function of the pupil size. Lens dimensions can include a preferred radius of the total lens, and may further include preferred thickness, or a preferred curvature of one or the other of the anterior surface and posterior surface of the lens.

A diffractive surface modeling module 1104 can receive information about the desired lens from the user input module 1102, and can determine aspects of a multizonal lens. For example, the modeling module 1104 can determine the shape of one or more echelettes of the diffractive profile of a diffractive multifocal lens, including the positioning, width, step height, and curvature needed to fulfill the multifocal prescription for each subset of the echelettes, as well as the positioning of each subset of echelettes. The multizonal diffractive surface modeling module 1104 can further determine the shapes of transition steps between echelettes. For example, transition steps may be smoothed or rounded to help mitigate optical aberrations caused by light passing through an abrupt transition. Such transition zone smoothing, which may be referred to as a low scatter profile, can provide for reductions in dysphotopsia by reducing the errant concentration of incident light behind the lens by the transition zones. By way of further example, echelette ordering, echelette offsets, and echelette boundaries may be adjusted to adjust the step heights between some adjacent echelettes.

The diffractive surface modeling module 1104 can be configured to generate performance criteria 1112, e.g. via modeling optical properties in a virtual environment. Performance criteria can include the match of the optical power profile of the multizonal lens with the desired optical power profile based on the extended range of vision prescription. The performance criteria can also include the severity of diffractive aberrations caused by lens surface. In some cases, the diffractive surface modeling module 1104 can provide a lens surface to a lens fabrication module for facilitating the production of a physical lens, which can be tested via a lens testing module 1110 for empirically determining the performance criteria 1112, so as to identify optical aberrations and imperfections not readily discerned via virtual modeling, and to permit iteration.

A refractive surface modeling module 1106 can receive information from the user input 1102 and diffractive surface modeling modules 1104 in order to determine refractive aspects of the lens. For example, provided with an extended range of vision prescription and a set of add powers that can be generated by a diffractive profile, the refractive surface modeling module 1106 can provide a refractive geometry configured to provide a base power which, when combined with the diffractive surface, meets the requirements of the multifocal lens prescription. The refractive surface modeling module 1106 can also generate performance criteria 1112, and can contribute to providing a lens surface to a lens fabrication module 1108 for facilitating the production of the physical lens.

Figure 12:
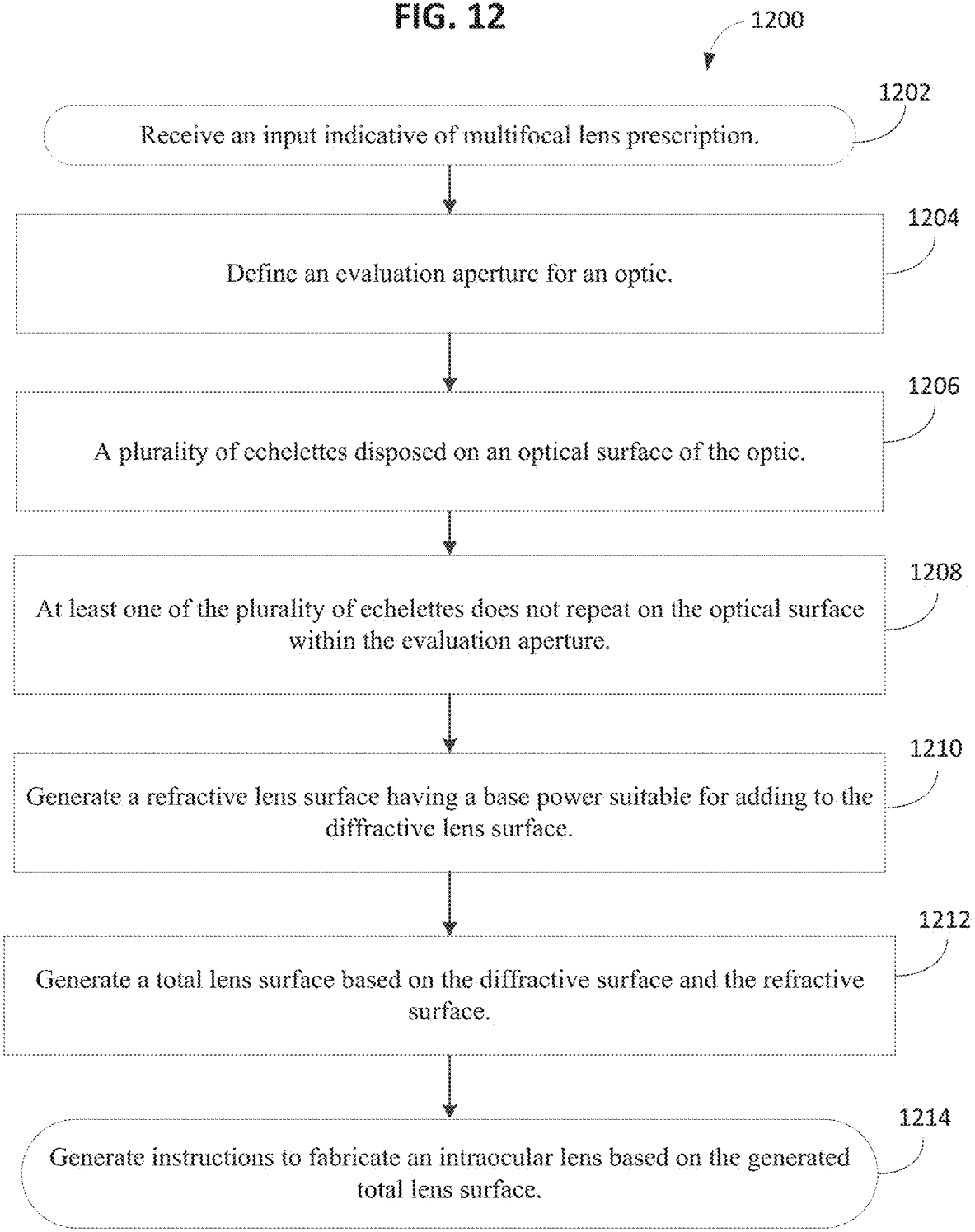
FIG. 12 illustrates an example process for generating a diffractive lens surface.

FIG. 12 is an example process 1200 for generating a diffractive lens surface, in accordance with embodiments. The process 1200 may be implemented in conjunction with, for example, the system 1100 shown in FIG. 11. In one embodiment, a process may be utilized to generate any diffractive lens surface disclosed or discussed in this application. Some or all of the process 1200 (or any other processes described herein, or variations, and/or combinations thereof) may be performed under the control of one or more computer systems configured with executable instructions, and may be implemented as code (e.g., executable instructions, one or more computer programs, or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

The process 1200 includes receiving an input indicative of a diffractive lens prescription (act 1202). The input can include, e.g., a desired optical power profile for correcting impaired distance vision, a desired optical power profile for correcting impaired intermediate distance vision, a desired optical power profile for accommodating near vision, and any suitable combination of the above. The process 1200 may also include defining an evaluation aperture for an optic (act 1204). Based on a desired optical power profile and the size and shape of the evaluation aperture. The generated diffractive profile may include a plurality of echelettes disposed on an optical surface of the optic (act 1206). At least one of the plurality of echelettes may not repeat on the optical surface within the evaluation aperture (act 1208).

The diffractive lens profile of the multizonal diffractive lens surface may be used in combination with a known refractive base power. To that end, a refractive lens surface may be generated having a base power that, in combination with the diffractive lens surface, meets the diffractive lens prescription (act 1210). A total lens surface can be generated based on both the refractive lens surface and the diffractive lens surface (act 1212). The refractive lens surface can include a refractive lens curvature on the anterior surface of the lens, the posterior surface of the lens, or both. Instructions can be generated to fabricate an intraocular lens based on the generated total lens surface (act 1214).

Figure 13:
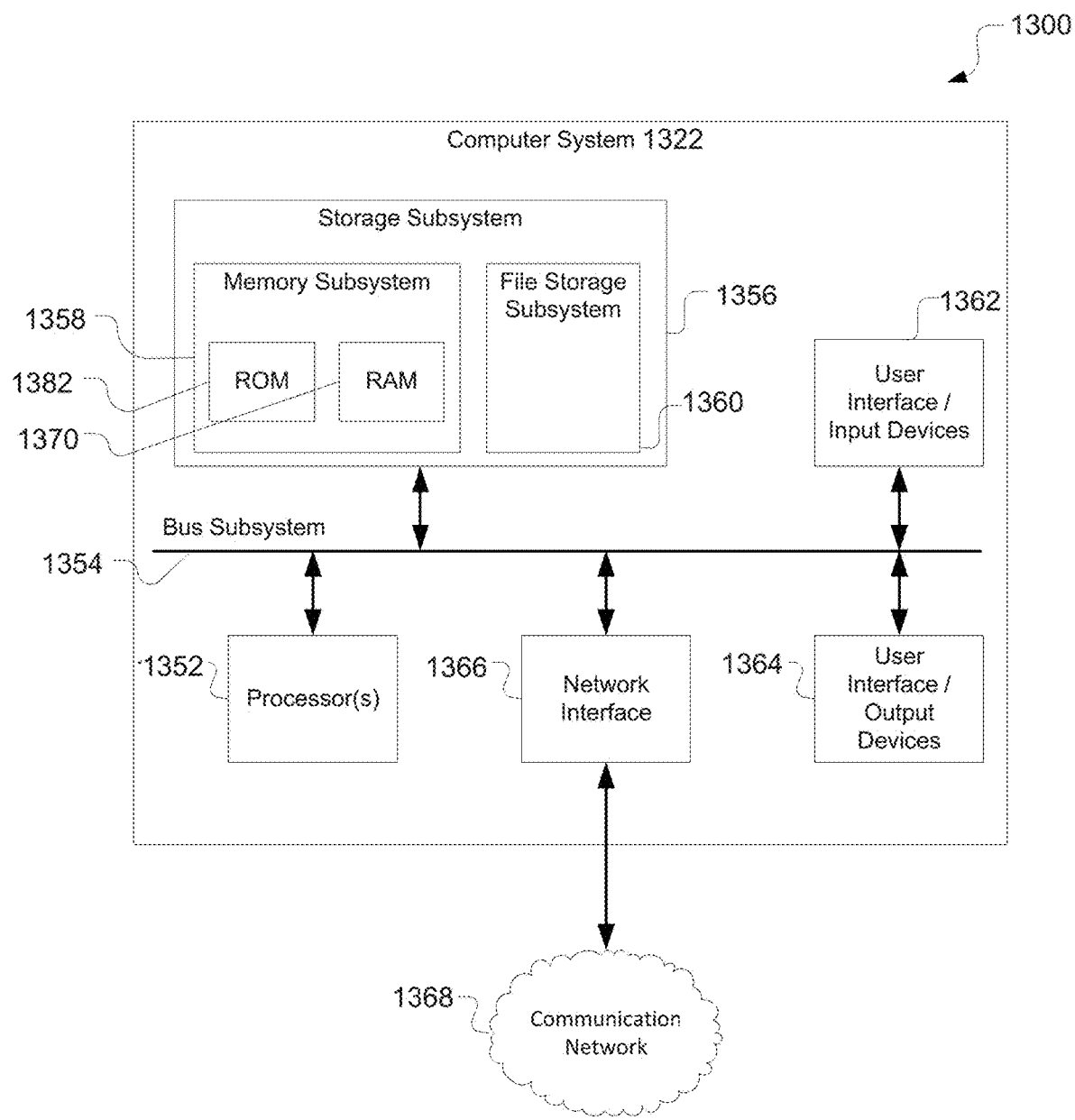
FIG. 13 illustrates an example computing environment for facilitating the systems and processes of FIGS. 11 and 12.

Computational Methods:

FIG. 13 is a simplified block diagram of an exemplary computing environment 1300 that may be used by systems for generating the continuous progressive lens surfaces of the present disclosure. Computer system 1322 typically includes at least one processor 1352 which may communicate with a number of peripheral devices via a bus subsystem 1354. These peripheral devices may include a storage subsystem 1356 comprising a memory subsystem 1358 and a file storage subsystem 1360, user interface input devices 1362, user interface output devices 1364, and a network interface subsystem 1366. Network interface subsystem 1366 provides an interface to outside networks 1368 and/or other devices, such as the lens fabrication module 1108 or lens testing module 1110 of FIG. 11.

User interface input devices 1362 may include a keyboard, pointing devices such as a mouse, trackball, touch pad, or graphics tablet, a scanner, foot pedals, a joystick, a touchscreen incorporated into the display, audio input devices such as voice recognition systems, microphones, and other types of input devices. User input devices 1362 will often be used to download a computer executable code from a tangible storage media embodying any of the methods of the present disclosure. In general, use of the term "input device" is intended to include a variety of conventional and proprietary devices and ways to input information into computer system 1322.

User interface output devices 1364 may include a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide a non-visual display such as via audio output devices. In general, use of the term "output device" is intended to include a variety of conventional and proprietary devices and ways to output information from computer system 1322 to a user.

Storage subsystem 1356 can store the basic programming and data constructs that provide the functionality of the various embodiments of the present disclosure. For example, a database and modules implementing the functionality of the methods of the present disclosure, as described herein, may be stored in storage subsystem 1356. These software modules are generally executed by processor 1352. In a distributed environment, the software modules may be stored on a plurality of computer systems and executed by processors of the plurality of computer systems. Storage subsystem 1356 typically comprises memory subsystem 1358 and file storage subsystem 1360. Memory subsystem 1358 typically includes a number of memories including a main random access memory (RAM) 1370 for storage of instructions and data during program execution.

Various computational methods discussed above, e.g. with respect to generating a multizonal lens surface, may be performed in conjunction with or using a computer or other processor having hardware, software, and/or firmware. The various method steps may be performed by modules, and the modules may comprise any of a wide variety of digital and/or analog data processing hardware and/or software arranged to perform the method steps described herein. The modules optionally comprising data processing hardware adapted to perform one or more of these steps by having appropriate machine programming code associated therewith, the modules for two or more steps (or portions of two or more steps) being integrated into a single processor board or separated into different processor boards in any of a wide variety of integrated and/or distributed processing architectures. These methods and systems will often employ a tangible media embodying machine-readable code with instructions for performing the method steps described above. Suitable tangible media may comprise a memory (including a volatile memory and/or a non-volatile memory), a storage media (such as a magnetic recording on a floppy disk, a hard disk, a tape, or the like; on an optical memory such as a CD, a CD-R/W, a CD-ROM, a DVD, or the like; or any other digital or analog storage media), or the like.

What is claimed is:

1. An ophthalmic lens comprising:
an optic including a first surface and a second surface each disposed about an optical axis and extending radially outward from the optical axis to an outer periphery of the optic, the first surface facing opposite the second surface and joining to the second surface at the outer periphery of the optic; and
a diffractive profile imposed on the first surface and including a plurality of echelettes and a plurality of transition zones, each transition zone of the plurality of transition zones being between adjacent echelettes of the plurality of echelettes, wherein at least one of the plurality of echelettes does not repeat on the first surface between the optical axis and the outer periphery of the optic, and wherein at least one transition zone of the plurality of transition zones connecting adjacent echelettes has a zero step height, wherein the echelettes connected by a zero step height have different parabolic profiles.

2. The ophthalmic lens of claim 1, wherein at least two of the plurality of echelettes each do not repeat on the first surface between the optical axis and the outer periphery of the optic.

3. The ophthalmic lens of claim 1, wherein at least three of the plurality of echelettes each do not repeat on the first surface between the optical axis and the outer periphery of the optic.

4. The ophthalmic lens of claim 1, wherein the plurality of echelettes includes at least three echelettes.

5. The ophthalmic lens of claim 1, wherein the plurality of echelettes includes at least one echelette that repeats on the first surface between the optical axis and the outer periphery of theoptic.

6. The ophthalmic lens of claim 1, wherein the plurality of echelettes includes a set of at least two echelettes, the set being repeated on the first surface between the optical axis and the outerperiphery of the optic.

7. The ophthalmic lens of claim 6, wherein the set being repeated on the first surface forms arepeated set, the repeated set being apodized.

8. An ophthalmic lens comprising:
an optical surface disposed about an optical axis, the optical surface including a central zone extending radially outward from the optical axis to a radial distance of 1.5 millimeters; and
a diffractive profile imposed on the optical surface, and including a plurality of echelettes and a plurality of transition zones disposed on the central zone, each transition zone of the plurality of transition zones being between adjacent echelettes of the plurality of echelettes, wherein at least one of the plurality of echelettes does not repeat on the central zone, and wherein at least one transition zone of the plurality of transition zones has a zero step height, wherein the echelettes connected by a zero step height have different parabolic profiles.

9. The ophthalmic lens of claim 8, wherein at least two of the plurality of echelettes each do notrepeat on the central zone.

10. The ophthalmic lens of claim 8, wherein at least three of the plurality of echelettes each do not repeat on the central zone.

11. The ophthalmic lens of claim 8, wherein each echelette on the central zone does not rep eaton the central zone.

12. The ophthalmic lens of claim 8, wherein the plurality of echelettes includes at least three echelettes disposed on the central zone.

13. The ophthalmic lens of claim 8, wherein the central zone is a first zone, and the optical surface includes a second zone extending radially outward from the central zone to an outerperiphery of the optical surface, and
the diffractive profile includes a plurality of echelettes disposed on the second zone, wherein at least one of the plurality of echelettes disposed on the second zone repeats on thesecond zone.

14. The ophthalmic lens of claim 13, wherein the plurality of echelettes disposed on the secondzone includes a set of at least two echelettes, the set being repeated on the second zone.

15. An ophthalmic lens comprising:
an optical surface disposed about an optical axis, the optical surface including a central zone extending radially outward from the optical axis to a radial distance of 2.5 millimeters; and
a diffractive profile imposed on the optical surface, and including a plurality of echelettes and a plurality of transition zones disposed on the central zone, each transition zone of the plurality of transition zones being between adjacent echelettes of the plurality of echelettes, wherein at least one of the plurality of echelettes does not repeat on the central zone, and wherein at least one transition zone of the plurality of transition zones connecting adjacent echelettes has a zero step height, wherein the echelettes connected by a zero step height have different parabolic profiles.

16. The ophthalmic lens of claim 15, wherein at least two of the plurality of echelettes each donot repeat on the central zone.

17. The ophthalmic lens of claim 15, wherein at least three of the plurality of echelettes each do not repeat on the central zone.

18. The ophthalmic lens of claim 15, wherein each echelette on the central zone does not repeat on the central zone.

19. The ophthalmic lens of claim 15, wherein the plurality of echelettes includes at least three echelettes disposed on the central zone.

20. The ophthalmic lens of claim 15, wherein the central zone is a first zone, and the optical surface includes a second zone extending radially outward from the central zone to an outerperiphery of the optical surface, and
the diffractive profile includes a plurality of echelettes disposed on the second zone, wherein at least one of the plurality of echelettes disposed on the second zone repeats on thesecond zone.

21. The ophthalmic lens of claim 20, wherein the plurality of echelettes disposed on the secondzone includes a set of at least two echelettes, the set being repeated on the second zone.

22. An ophthalmic lens comprising:
an optic including a first surface and a second surface each disposed about an optical axis and extending radially outward from the optical axis to an outer periphery of the optic, the first surface facing opposite the second surface and joining to the second surface at the outer periphery of the optic; and
a diffractive profile imposed on the first surface and including a plurality of echelettes and a plurality of transition zones, each transition zone of the plurality of transition zones being between adjacent echelettes of the plurality of echelettes, wherein at least one of the plurality of echelettes has a profile in r-squared space that is different than a profile in r-squared space of any other echelette that is disposed on the first surface between the optical axis and the outer periphery of the optic, and wherein at least one transition zone of the plurality of transition zones connecting adjacent echelettes has a zero step height, wherein the adjacent echelettes connected by a zero step height have different parabolic profiles.

23. The ophthalmic lens of claim 22, wherein at least three echelettes are disposed on the first surface between the optical axis and the outer periphery of the optic.

24. The ophthalmic lens of claim 22, wherein at least two of the plurality of echelettes disposed on the first surface between the optical axis and the outer periphery of the optic each has a profilein r-squared space that is different than a profile in r-squared space of any other echelette that is disposed on the first surface between the optical axis and the outer periphery of the optic.

25. The ophthalmic lens of claim 22, wherein at least three of the plurality of echelettes disposed on the first surface between the optical axis and the outer periphery of the optic each has a profilein r-squared space that is different than a profile in r-squared space of any other echelette that is disposed on the first surface between the optical axis and the outer periphery of the optic.

26. The ophthalmic lens of claim 22, wherein the plurality of echelettes includes at least one echelette that repeats on the first surface between the optical axis and the outer periphery of the optic.

27. The ophthalmic lens of claim 22, wherein the plurality of echelettes includes a set of at least two echelettes, the set being repeated on the first surface between the optical axis and the outer periphery of the optic.

28. An ophthalmic lens comprising:
an optical surface disposed about an optical axis, the optical surface including a central zone extending radially outward from the optical axis to a radial distance of 1.5 millimeters; and
a diffractive profile imposed on the optical surface, and including a plurality of echelettes and a plurality of transition zones disposed on the central zone, each transition zone of the plurality of transition zones being between adjacent echelettes of the plurality of echelettes, wherein
at least one of the plurality of echelettes on the central zone has a profile in r-squared space that is different than a profile in r-squared space of any other echelette that is on the centralzone, and wherein
at least one transition zone of the plurality of transition zones connecting adjacent echelettes has a zero step height, wherein the adjacent echelettes connected by a zero step height have different parabolic profiles.

29. The ophthalmic lens of claim 28, wherein at least three echelettes are disposed on the central zone.

30. The ophthalmic lens of claim 28, wherein at least two of the plurality of echelettes on the central zone each has a profile in r-squared space that is different than a profile in r-squared space of any other echelette that is on the central zone.

31. The ophthalmic lens of claim 28, wherein at least three of the plurality of echelettes on the central zone each has a profile in r-squared space that is different than a profile in r-squared space of any other echelette that is on the central zone.

32. The ophthalmic lens of claim 28, wherein the central zone is a first zone, and the optical surface includes a second zone extending radially outward from the central zone to an outerperiphery of the optical surface, and
the diffractive profile includes a plurality of echelettes disposed on the second zone, wherein at least one of the plurality of echelettes disposed on the second zone repeats on thesecond zone.

33. The ophthalmic lens of claim 28, wherein the plurality of echelettes disposed on the secondzone includes a set of at least two echelettes, the set being repeated on the second zone.

34. An ophthalmic lens comprising:
an optical surface disposed about an optical axis, the optical surface including a central zone extending radially outward from the optical axis to a radial distance of 2.5 millimeters; and
a diffractive profile imposed on the optical surface, and including a plurality of echelettes and a plurality of transition zones disposed on the central zone, each transition zone of the plurality of transition zones being between adjacent echelettes of the plurality of echelettes, wherein
at least one of the plurality of echelettes on the central zone has a profile in r-squared space that is different than a profile in r-squared space of any other echelette that is on the centralzone, and wherein
at least one transition zone of the plurality of transition zones has a zero step height, and
the echelettes adjacent to the transition zone with a zero step height have different parabolic profiles.

35. The ophthalmic lens of claim 34, wherein at least three echelettes are disposed on the centralzone.

36. The ophthalmic lens of claim 34, wherein at least two of the plurality of echelettes on the central zone each has a profile in r-squared space that is different than a profile in r-squared space of any other echelette that is on the central zone.

37. The ophthalmic lens of claim 34, wherein at least three of the plurality of echelettes on the central zone each has a profile in r-squared space that is different than a profile in r-squared space of any other echelette that is on the central zone.

38. The ophthalmic lens of claim 34, wherein the central zone is a first zone, and the optical surface includes a second zone extending radially outward from the central zone to an outerperiphery of the optical surface, and
the diffractive profile includes a plurality of echelettes disposed on the second zone, wherein at least one of the plurality of echelettes disposed on the second zone repeats on thesecond zone.

39. The ophthalmic lens of claim 38, wherein the plurality of echelettes disposed on the second zone includes a set of at least two echelettes, the set being repeated on the second zone.

40. A method of designing an intraocular lens, the method comprising:
defining an evaluation aperture for an optic;
defining a diffractive profile including:
a plurality of echelettes and a plurality of transition zones disposed on an optical surface of the optic, each transition zone of the plurality of transition zones being between adjacent echelettes of the plurality of echelettes, at least one of the plurality of echelettes does not repeat on the optical surfacewithin the evaluation aperture;

at least one transition zone of the plurality of transition zones connecting adjacent echelettes of the plurality of echelettes has a zero step height;

wherein the echelettes connected by a zero step height have different parabolic profiles; and generating a diffractive lens surface based on the diffractive profile.

41. The method of claim 40, wherein the evaluation aperture comprises a zone extending radially outward from an optical axis of the optic to a radial distance of 1.5 millimeters.

42. The method of claim 40, wherein the evaluation aperture comprises a zone extending radially outward from an optical axis of the optic to a radial distance of 2.5 millimeters.

43. The method of claim 40, wherein the evaluation aperture comprises an annular zonedisposed about an optical axis of the optic.

44. A manufacturing system for making an ophthalmic lens, the system comprising:

an input that accepts an ophthalmic lens prescription for a patient eye;

a first module configured to generate a diffractive profile based on the ophthalmic lens prescription, wherein the diffractive profile includes:

a plurality of echelettes and a plurality of transition zones disposed on an optical surface, each transition zone of the plurality of transition zones being between adjacent echelettes of the plurality of echelettes, at least one of the plurality of echelettes does not repeat on the optical surfacewithin an evaluation aperture; and at least one transition zone of the plurality of transition zones connecting adjacent echelettes of the plurality of echelettes has a zero step height;

wherein the echelettes connected by a zero step height have different parabolic profiles; and a manufacturing assembly that fabricates the ophthalmic lens based on the diffractive profile.

45. The manufacturing system of claim 44, wherein the optical surface is disposed about an optical axis, and the evaluation aperture comprises a zone on the optical surface extending radially outward from the optical axis to a radial distance of 1.5 millimeters.

46. The manufacturing system of claim 44, wherein the optical surface is disposed about an optical axis, and the evaluation aperture comprises a zone on the optical surface extending radially outward from the optical axis to a radial distance of 2.5 millimeters.

47. The manufacturing system of claim 44, wherein the optical surface is disposed about an optical axis, and the evaluation aperture comprises an annular zone on the optical surface disposed about an optical axis of the optic.

48. An ophthalmic lens comprising:

an optical surface disposed about an optical axis; and a diffractive profile imposed on the optical surface, and including a plurality of echelettes and a plurality of transition zones, each transition zone of the plurality of transition zones being between adjacent echelettes of the plurality of echelettes, and one of the plurality of echelettes:

is repeated on the optical surface, does not form part of a set of adjacent echelettes that repeats on the optical surface, and is not repeated in any adjacent echelette, and at least one transition zone of the plurality of transition zones connecting adjacent echelettes of the plurality of echelettes has a zero step height, wherein the echelettes connected by a zero step height have different parabolic profiles.

49. The ophthalmic lens of claim 48, wherein the one of the plurality of echelettes is repeated onthe optical surface at least twice.

50. The ophthalmic lens of claim 48, wherein the optical surface is a first surface of an optic, and the optic includes a second surface disposed about the optical axis, the first surface and the second surface each extending radially outward from the optical axis to an outer periphery of theoptic, the first surface facing opposite the second surface and joining to the second surface at the outer periphery of the optic.

51. The ophthalmic lens of claim 50, wherein the plurality of echelettes includes at least one echelette that does not repeat on the first surface between the optical axis and the outer periphery of the optic.

52. The ophthalmic lens of claim 50, wherein the plurality of echelettes includes at least two echelettes that each do not repeat on the first surface between the optical axis and the outer periphery of the optic.

53. The ophthalmic lens of claim 48, wherein the plurality of echelettes includes a set of at least two adjacent echelettes, the set of at least two adjacent echelettes being repeated on the optical surface.

54. An ophthalmic lens comprising:

an optical surface disposed about an optical axis; and a diffractive profile imposed on the optical surface, and including a plurality of echelettes and a plurality of transition zones, each transition zone of the plurality of transition zones being between adjacent echelettes of the plurality of echelettes, at least two adjacent echelettes of the plurality of echelettes forming a set of echelettes, and the set:

does not form part of a greater set of adjacent echelettes that repeats on the opticalsurface, is repeated on the optical surface to form one or more multiples of the set on theoptical surface, and is separated from each of the one or more multiples of the set by at least one echelette, and wherein at least one transition zone of the plurality of transition zones connecting adjacent echelettes of the plurality of echelettes has a zero step height, and wherein the echelettes connected by a zero step height have different parabolic profiles.

55. The ophthalmic lens of claim 54, wherein the set is repeated on the optical surface to form atleast two multiples of the set on the optical surface.

56. The ophthalmic lens of claim 54, wherein the set is separated from each of the one or moremultiples of the set by at least two echelettes.

57. The ophthalmic lens of claim 54, wherein at least three adjacent echelettes of the plurality ofechelettes form the set of echelettes.

58. The ophthalmic lens of claim 54, wherein the optical surface is a first surface of an optic, and the optic includes a second surface disposed about the optical axis, the first surface and the second surface each extending radially outward from the optical axis to an outer periphery of theoptic, the first surface facing opposite the second surface and joining to the second surface at the outer periphery of the optic.

59. The ophthalmic lens of claim 58, wherein the plurality of echelettes includes at least one echelette that does not repeat on the first surface between the optical axis and the outer periphery of the optic.

60. A method of designing an intraocular lens, the method comprising:
- defining a diffractive profile including a plurality of echelettes and a plurality of transition zones disposed on an optical surface, each transition zone of the plurality of transition zones being between adjacent echelettes of the plurality of echelettes, and one of the plurality of echelettes:
  - is repeated on the optical surface,
  - does not form part of a set of adjacent echelettes that repeats on the optical surface, and
  - is not repeated in any adjacent echelette;
- at least one transition zone of the plurality of transition zones connecting adjacent echelettes of the plurality of echelettes has a zero step height;
- wherein the echelettes connected by a zero step height have different parabolic profiles; and
- generating a diffractive lens surface based on the diffractive profile.

61. A method of designing an intraocular lens, the method comprising:
- defining a diffractive profile including a plurality of echelettes and a plurality of transition zones disposed on an optical surface, each transition zone of the plurality of transition zones being between adjacent echelettes of the plurality of echelettes, at least two adjacent echelettes of the plurality of echelettes forming a set of echelettes, and the set:
  - does not form part of a greater set of adjacent echelettes that repeats on the optical surface,
  - is repeated on the optical surface to form one or more multiples of the set on the optical surface, and
  - is separated from each of the one or more multiples of the set by at least one echelette;
- at least one transition zone of the plurality of transition zones connecting adjacent echelettes of the plurality of echelettes has a zero step height;
- wherein the echelettes connected by a zero step height have different parabolic profiles and
- generating a diffractive lens surface based on the diffractive profile.

62. A manufacturing system for making an ophthalmic lens, the system comprising:
- an input that accepts an ophthalmic lens prescription for a patient eye;
- a first module configured to generate a diffractive profile based on the ophthalmic lens prescription, wherein the diffractive profile includes:
  - a plurality of echelettes and a plurality of transition zones disposed on an optical surface, each transition zone of the plurality of transition zones being between adjacent echelettes of the plurality of echelettes, and one of the plurality of echelettes:
    - is repeated on the optical surface,
    - does not form part of a set of adjacent echelettes that repeats on the opticalsurface, and
    - is not repeated in any adjacent echelette;
  - and wherein at least one transition zone of the plurality of transition zones connecting adjacent echelettes of the plurality of echelettes has a zero step height;
  - wherein the echelettes connected by a zero step height have different parabolic profiles; and
- a manufacturing assembly that fabricates the ophthalmic lens based on the diffractive profile.

63. A manufacturing system for making an ophthalmic lens, the system comprising: an input that accepts an ophthalmic lens prescription for a patient eye;
- a first module configured to generate a diffractive profile based on the ophthalmic lensprescription, wherein the diffractive profile includes:
  - a plurality of echelettes and a plurality of transition zones disposed on an optical surface, each transition zone of the plurality of transition zones being between adjacent echelettes of the plurality of echelettes, at least two adjacent echelettes of the plurality of echelettes forming a set of echelettes, and the set:
    - does not form part of a greater set of adjacent echelettes that repeats on theoptical surface,
    - is repeated on the optical surface to form one or more multiples of the seton the optical surface, and
    - is separated from each of the one or more multiples of the set by at leastone echelette;
- at least one transition zone of the plurality of transition zones connecting adjacent echelettes of the plurality of echelettes has a zero step height;
- wherein the echelettes connected by a zero step height have different parabolic profiles and
- a manufacturing assembly that fabricates the ophthalmic lens based on the diffractive profile.

* * * * *